US010526643B2

(12) United States Patent
Dahl et al.

(10) Patent No.: US 10,526,643 B2
(45) Date of Patent: *Jan. 7, 2020

(54) MULTIPLEX DETECTION OF NUCLEIC ACIDS

(71) Applicant: Vanadis Diagnostics, Sollentuna (SE)

(72) Inventors: Carl Oscar Fredrik Dahl, Sigtuna (SE); Olof John Ericsson, Uppsala (SE)

(73) Assignee: Vanadis Diagnostics, Sollentuna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/036,778

(22) PCT Filed: Nov. 26, 2014

(86) PCT No.: PCT/IB2014/003062
§ 371 (c)(1),
(2) Date: May 13, 2016

(87) PCT Pub. No.: WO2015/083002
PCT Pub. Date: Jun. 11, 2015

(65) Prior Publication Data
US 2016/0281130 A1 Sep. 29, 2016

(30) Foreign Application Priority Data
Dec. 2, 2013 (GB) .................................. 1321196.6

(51) Int. Cl.
*C12Q 1/682* (2018.01)
(52) U.S. Cl.
CPC .................................. *C12Q 1/682* (2013.01)
(58) Field of Classification Search
CPC combination set(s) only.
See application file for complete search history.

(56) References Cited

U.S. PATENT DOCUMENTS

| 5,854,033 | A | 12/1998 | Lizardi et al. | |
|---|---|---|---|---|
| 6,316,229 | B1 * | 11/2001 | Lizardi | C12Q 1/682 435/6.1 |
| 2004/0166514 | A1 | 8/2004 | Puskas | |
| 2007/0087355 | A1 | 4/2007 | Barrett | |
| 2009/0004701 | A1 | 1/2009 | Faham et al. | |
| 2013/0275103 | A1 | 10/2013 | Struble et al. | |

FOREIGN PATENT DOCUMENTS

| EP | 2653559 | 10/2013 | | |
|---|---|---|---|---|
| GB | 2492042 | 5/2011 | | |
| GB | 2492042 | 12/2012 | | |
| RU | 2478716 C2 | 4/2013 | | |
| WO | 03012119 A2 † | 2/2003 | | |
| WO | 2001094625 | 3/2003 | | |
| WO | 2003044216 | 5/2003 | | |
| WO | 2005047547 | 5/2005 | | |
| WO | 2005111236 | 11/2005 | | |
| WO | 2005111236 A1 † | 11/2005 | | |
| WO | 20070087355 | 4/2007 | | |
| WO | 2009029742 | 3/2009 | | |
| WO | 2011009941 | 1/2011 | | |
| WO | WO 2011068909 A2 * | 6/2011 | .......... | C12N 15/115 |
| WO | 2011142836 | 11/2011 | | |
| WO | 2011142836 A2 † | 11/2011 | | |
| WO | 2012019200 A2 † | 2/2012 | | |
| WO | WO 2012019200 A2 * | 2/2012 | .......... | C12Q 1/6827 |
| WO | 2012019200 | 11/2012 | | |
| WO | 2013079649 | 6/2013 | | |
| WO | 2013/109981 A1 | 7/2013 | | |
| WO | 2013/132305 A1 | 9/2013 | | |
| WO | 2013/150503 A1 | 10/2013 | | |
| WO | 2014165267 | 12/2014 | | |
| WO | 2015083001 | 6/2015 | | |
| WO | 2015083002 | 6/2015 | | |

OTHER PUBLICATIONS

Goransson (Nucleic Acids Research (2009) vol. 37, e7 and supplemental content).*
Maruyama ( Applied and Environmental Microbiology (2005) vol. 71, pp. 7933-7940).*
Abalsan (Methods in Molecular Biology (2007) vol. 396, pp. 315-330).*
Amann, et al., "Combination of 16S rRNA-Targeted Oligonucleotide Probes with Flow Cytometry for Analyzing Mixed Microbial Populations", Applied and Environmental Microbiology, 1990, 56(6): 1919-1925.
Eriksson, et al., "Multiplex and quantifiable detection of nucleic acid from pathogenic fungi using padlock probes, generic real time PCR and specific suspension array readout", Journal of Microbiological Methods, 2009, 78: 195-202.
Nilsson, et al., "Real-time monitoring of rolling-circle amplification using a modified molecular beacon design", Nucleic Acids Research, 2002, 30(14): e66.
Zhou, et al., "Two-color, rolling-circle amplification on antibody microarrays for sensitive, multiplexed serum-protein measurements", Genome Biology, 2004, 5:R28.
Third Party Observations filed against European Patent Application No. 14863081.7, dated Apr. 4, 2017.

(Continued)

*Primary Examiner* — Steven Pohnert
(74) *Attorney, Agent, or Firm* — James S. Keddie; Bozicevic, Field & Francis LLP

(57) ABSTRACT

Described herein is a new approach in which a nucleic acid species of interest (e.g. a chromosome) containing multiple unique target sequences is detected using multiple specific probes that are amplified by rolling circle amplification and detected. Multiple probes are used to provide a detectable signal, where the magnitude of the signal is proportional to the number of probes recognising their target sequences. Individual signals from the plurality of probes are converted into a single cumulative detectable signal, amplifying the individual signals through the multiplex probing. Ten or more probes produce a signal amplification of ten-fold or more. The generated signals depend on correctly reacted probes upon target recognition, using sequence specific hybridisation and enzymatic catalysis to generate specific products from which the signal is obtained.

15 Claims, 8 Drawing Sheets
Specification includes a Sequence Listing.

(56) References Cited

OTHER PUBLICATIONS

Third Party Observations filed against United Kingdom Patent Application No. 1321196.6 (GB2520765), dated Apr. 11, 2017.

Hardenbol et al., "Multiplexed genotyping with sequence-tagged molecular inversion probes" Nat Biotechnol, Jun. 2003, pp. 673-678, vol. 21, No. 6.

Dahl et al., "Multiplex amplification enabled by selective circularization of large sets of genomic DNA fragments" Nucleic Acids Res, Apr. 2005, p. e71, vol. 33, No. 8.

Fredriksson et al., "Multiplex amplification of all coding sequences within 10 cancer genes by Gene-Collector" Nucleic Acids Res, Apr. 2007, p. e47, vol. 35, No. 7.

Guo et al., "Simultaneous Detection of Trisomies 13, 18, and 21 with Multiplex Litigation-Dependent Probe Amplification-Based Real-Time PCR" Clinical Chemistry, Sep. 2010, pp. 1451-1459, vol. 56, No. 9.

Hardenbol et al., "Highly multiplexed molecular inversion probe genotyping: over 10,000 targeted SNP's genotyped in a single tube assay" Genome Res, Feb. 2005, pp. 269-275, vol. 15, No. 2.

Marciniak et al., "Coupled rolling circle amplification loop-mediated amplification for rapid detection of short DNA sequences" BioTechniques, Sep. 2008, pp. 275-280, vol. 45, No. 3.

Shen et al., "Multiplex target capture with double-stranded DNA probes" Genome Med, 2013, p. 50, vol. 5, No. 5.

Nakao et al., Highly Specific Zept-Mole Level DNA Detection by Combination of Thermal Lens Microscope and Rolling Circle Amplification; 16th International Conference on Miniaturized Systems for Chemistry and Life Sciences, Oct. 28-Nov. 1, 2012, Okinawa, Japan.†

Lizardi et al., "Mutation Detection and Single-molecule Counting Using Isothermal Rolling-circle Amplification", Nature Genetics, 1998, 19, 225-232.†

Yaroslavsky et al.; "Fluorescence Imaging of Single-copy DNA Sequences within the Human Genome Using PNA-directed Padlock Probe Assembly"; Chem Biol. 2013, 20(3), 445-453.†

Jarvius et al., "Digital Quantification Using Amplified Single-molecule Detection", Nature Methods, 2006, 3(9), 725-727.†

Goransson et al.; "A Single Molecule Array for Digital Targeted Molecular Analysis"; Nucleic Acids Research, 2009, 37(1), e7.†

\* cited by examiner
† cited by third party

SEQUENCE LISTING

<160> NUMBER OF SEQ ID NOS: 3

<210> SEQ ID NO 1
<211> LENGTH: 93
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (31)..(60)
<223> OTHER INFORMATION: positions 31 to 60 represent a target
      complementary sequence on human chromosome 21.

<400> SEQUENCE: 1
atgtgaccct tccgtctgtt gagttaggcc nnnnnnnnnn nnnnnnnnnn nnnnnnnnnn     60
tcgtgccttg tcattcggga gcactaactg ctg                                 93

<210> SEQ ID NO 2
<211> LENGTH: 152
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: c has 5' phosphate
<220> FEATURE:
<221> NAME/KEY: misc_feature
<222> LOCATION: (64)..(73)
<223> OTHER INFORMATION: n is a, c, g, or t

<400> SEQUENCE: 2
cgcacacgat taaggtccag tcacaggcag agatcggaag agcgtcgtgt agggaaagag     60
tgtnnnnnnn nnngtgtaga tctcggtggt cgccgtatca tttcatgctg ctaacggtcg    120
agtcggacag gtggctccac taaatagacg ca                                  152

<210> SEQ ID NO 3
<211> LENGTH: 152
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: g has a 5' phosphate
<220> FEATURE:
<221> NAME/KEY: misc_feature
<222> LOCATION: (64)..(73)
<223> OTHER INFORMATION: n is a, c, g, or t

<400> SEQUENCE: 3
ggcctaactc aacagacgga agggtcacat agatcggaag agcgtcgtgt agggaaagag     60
tgtnnnnnnn nnngtgtaga tctcggtggt cgccgtatca tttcatgctg ctaacggtcg    120
agcagttagt gctcccgaat gacaaggcac ga                                  152
```

MULTIPLEX DETECTION OF NUCLEIC ACIDS

CROSS-REFERENCING

This application is a § 371 filing of PCT/IB2014/003062, filed on Nov. 26, 2014, which claims the benefit of UK Application No: 1321196.6, filed on Dec. 2, 2013, which applications are incorporated by reference herein.

FIELD OF THE INVENTION

The invention relates to multiplex methods of detecting multiple nucleic acid sequences in parallel using probes that bind specific sequences. The invention also relates to quantification of species of nucleic acid, for example determining the relative quantities of two different chromosomes in a sample, including use of such methods in non-invasive pre-natal diagnosis of foetal aneuploidies.

BACKGROUND

Many diseases are caused or characterised by an imbalance in the number of chromosomes (aneuploidy) or an imbalance in the number of chromosomal segments (partial aneuploidy) in cells of an individual compared with the normal number of chromosomes or chromosomal segments for the species. The human diploid genome has 23 pairs of chromosomes; paired chromosomes 1 to 22 and the sex chromosomes XX or XY. The terms monosomy and trisomy refer to a missing or extra chromosome, while partial monosomy and partial trisomy refer to an imbalance of genetic material caused by loss or gain respectively of part of a chromosome. Aneuploidy and partial aneuploidy in an individual's genome are associated with congenital disorders such as Down's syndrome (trisomy of human chromosome 21) and Turner syndrome (monosomy or partial monosomy of the sex chromosome). Aneuploidy and partial aneuploidy may also arise through somatic mutation in adult tissues. For example, many cancer cells exhibit chromosomal fragility leading to translocations of chromosomal fragments and aneuploidy of tumour cells.

Methods have been developed for diagnosing diseases associated with chromosomal defects. Traditional methods of karyotyping included obtaining a tissue sample, staining the chromosomes and examining them under a light microscope. Schröck et al. (Science 273(5274):494-497 1996) described multicolour spectral karyotyping, using fluorescence in situ hybridisation (FISH) to simultaneously visualise all human chromosomes in different colours. Fluorescently labelled probes were made for each chromosome by labelling chromosome-specific DNA with different fluorophores. Because there are a limited number of spectrally distinct fluorophores, a combinatorial labelling method was used to generate the required number of different emission spectra. Spectral differences generated by combinatorial labelling were captured and analysed using an interferometer attached to a fluorescence microscope. Image processing software then assigned a colour to each spectrally different combination, allowing the visualisation of the individually coloured chromosomes.

Comparative genomic hybridisation (CGH) involves the isolation of DNA from the two sources to be compared, most commonly a test and reference source, independent labelling of each DNA sample with fluorophores of different colours (usually red and green), denaturation of the DNA so that it is single stranded, and the hybridisation of the two resultant samples in a 1:1 ratio to a normal metaphase spread of chromosomes, to which the labelled DNA samples will bind at their locus of origin. Using a fluorescence microscope and computer software, the differentially coloured fluorescent signals are then compared along the length of each chromosome for identification of chromosomal differences between the two sources. A higher intensity of the test sample colour in a specific region of a chromosome indicates the gain of material of that region in the corresponding source sample, while a higher intensity of the reference sample colour indicates the loss of material in the test sample in that specific region. A neutral colour (yellow when the fluorophore labels are red and green) indicates no difference between the two samples in that location. CGH was described by Kallioniemi et al., Science 258(5083):818-21 1992 and Pinkel et al., Nat Genet. 20(2):207-11 1998.

More recently, digital or virtual karyotyping methods have been developed to quantify copy number on a genomic scale (Wang et al., PNAS 99(25):16156-16161 2002). Digital karyotyping allows differences in copy number to be detected at higher resolution compared with conventional karyotyping or chromosome-based CGH. Short sequences of DNA from specific loci all over the genome are isolated and enumerated. Tags of 21 bp each can be obtained from specific locations in the genome and generally contain sufficient information to uniquely identify the genomic loci from which they were derived. Tags can thus be matched to precise chromosomal locations and tag densities can be evaluated over moving windows to detect abnormalities in DNA sequence content. Methods of matching the sequence tags to their chromosomal locations include high throughput sequencing, use of array-comparative genomic hybridisation and SNP arrays.

Arrays are composed of hundreds to millions of probes which are complementary to a region of interest in the genome. DNA from the test sample is fragmented, labelled, and hybridised to the array. The hybridisation signal intensities for each probe are quantified for each position on the array. Knowing the address of each probe on the array and the address of each probe in the genome, an algorithm is used to line up the probes in chromosomal order and reconstruct the genome in silico. The resolution of digital karyotyping depends on the density of probes on the array.

One area where high precision analysis is required is in non-invasive prenatal karyotyping. Pregnant mothers carry cell-free circulating DNA in their blood, of which 4-30% is derived from the foetus. It is possible to determine the karyotype of the foetus by determining the abundance of cell free DNA originating from each chromosome. For example, if the cell free DNA consists of 95% maternal and 5% foetal DNA, and if the foetus has trisomy of chromosome 21 (Down's syndrome) then the total amount of cell free DNA from chromosome 21 should exceed that of any other genomic region of the same size by 2.5%. Observing a chromosomal aneuploidy in the foetal DNA requires a very precise measurement to detect such slight imbalances in the relative quantities of different chromosomes. The difficulty is compounded by a need to work with relatively small samples in order to provide a method that is convenient and acceptable for patients and clinicians.

Analysis of specific targets from single or a few DNA molecules has traditionally been a technical challenge. Methods to copy DNA are typically required to achieve sufficient signal for downstream analysis procedures. Analysis methods such as DNA sequencing, gel electrophoresis, and DNA microarrays typically require a signal amplification of the DNA in the sample provided. The most common amplification method to amplify specific DNA targets is PCR, which can provide millions (or billions) of copies of specific targets from a DNA sample. However, when it is desired to amplify many regions of a genomic sample for analysis, amplification artefacts can arise as a result of performing multiple different amplifications together in the same reaction mixture. Also, an amplification step can result in loss of information regarding relative quantities of sequences in the sample, since the original difference in relative quantity may be tiny compared with the absolute magnitude of the amplified nucleic acid products, and since different sequences may be amplified with different efficiencies.

SUMMARY OF THE INVENTION

Some embodiments of the method described herein introduce a novel approach in which a nucleic acid species of interest (e.g. a chromosome) containing multiple unique target sequences is detected using multiple specific probes. Multiple probes are used to provide a detectable signal, where the magnitude of the signal is proportional to the number of probes recognising their target sequences. Individual signals from the plurality of probes are converted into a single cumulative detectable signal, amplifying the individual signals through the multiplex probing. Ten or more probes produce a signal amplification of ten-fold or more. The generated signals depend on correctly reacted probes upon target recognition, using sequence specific hybridisation and enzymatic catalysis to generate specific products from which the signal is obtained.

Some embodiments use detection of multiple loci on a nucleic acid species of interest target molecule as a signal amplification step, and therefore enables signal generation and detection without requiring amplification of the products of the reacted probes. The signal from the multiplex products may however be optionally amplified by traditional signal amplification steps. Clonal amplification of the signal may be performed. Suitable amplification techniques include rolling circle amplification, bridge PCR, emPCR and digital PCR.

Each probe that recognises its target sequence generates a ligation product, and the ligation products produced by each probe hybridisation may be individually detectable, so that an individual signal is obtainable from each. However, an elegant feature of some implementations of the present method is that these individual signals need not be individually detected, but instead are merged into a cumulative signal and the cumulative signal is detected. The cumulative signal is a combination of the individual signals and can thus be used to detect and/or quantify the ligation products, representing the presence or quantity of the nucleic acid species under investigation. This allows an earlier merging of the probe signals compared with methods involving sequencing and microarrays, in which individual signals are generated for multiple probes across a region and then the signal is merged in the analysis to represent a region. The signal can be merged before detection, so that individual signals are not separately mapped or interrogated. This enables a simpler readout format.

The method of signal amplification by multiplexing can be used to detect nucleic acid species of interest in a sample, for example where a nucleic acid species is a minor or trace component in a complex nucleic acid sample. The amplification by multiplexing enables reliable detection. This may be used for example to detect microbial nucleic acid in samples, such as patient samples, for diagnostic purposes. Samples may be probed with probes specific for microbial nucleic acids of multiple species, to detect and identify those present. This is useful for detection of agents of infectious disease, such as bacteria, viruses and fungi. Specific nucleic acid transcripts may be detected. Amplification by multiplexing may also be used to quantify the nucleic acid species. By probing two or more species of nucleic acid—one or more species of interest and one or more reference nucleic acid species—the present method enables quantification of the relative amounts of the two species in the sample. The method is especially useful when applied to the detection or quantification of chromosomes or chromosomal loci, for example for chromosomal copy number detection. An application of particular value is the use of such methods for identifying chromosomal defects, including for the diagnosis of cancers and congenital aneuploidies. Use for non-invasive prenatal diagnosis (NIPT) is specifically described. The present method is of particular use when large nucleic acids that comprise a multitude of target sequences are interrogated/detected, especially if these nucleic acids are present in a low molar amount, and when they must measured or quantified with very high precision, as is the case in NIPT.

A species of nucleic acid in a sample may be detected by contacting the sample with a set of probes, wherein each probe specifically recognises a distinct target sequence in the species of nucleic acid to be detected, and wherein recognition of each target sequence by each probe generates a product, and detecting a cumulative signal which is a combination of the signals from the products, wherein detection of the signal indicates the presence of the species of nucleic acid in the sample. The species of nucleic acid may be quantified by quantifying the cumulative signal to determine a signal level, wherein the signal level is proportional to the quantity of the species of nucleic acid in the sample, and thereby determining the quantity of the species of nucleic acid in the sample. A first species of nucleic acid may be quantified relative to a second or reference species of nucleic acid by contacting the sample with a first set of probes and a second set of probes, wherein the probes of the first set each specifically recognise a distinct target sequence within the first species of nucleic acid and wherein the probes of the second set each specifically recognise a distinct target sequence within the second or reference species of nucleic acid. First and second cumulative signals are detected, the first cumulative signal being a combination of individual signals from products generated by probes of the first set recognising their target sequences, and the second cumulative signal being a combination of individual signals from products generated by probes of the second set recognising their target sequences. The first and second signals are quantified to determine first and second signal levels respectively, these being proportional to the quantities of the first and second species of nucleic acid in the sample. The relative quantities of the first and second nucleic acid species in the sample may thus be determined by comparing the first and second signal levels.

For example, the cumulative signal may be the summarised enumeration of clonally amplified and/or labelled products of the probes that recognise their target sequences, for example products of rolling circle amplification, or a fluorescent signal emitted from all the products where each product emits a fluorescent signal. For quantifying relative amounts of multiple species of nucleic acids, different signals are used for each species, for example products of one set of probes may emit a different wavelength or spectrum of fluorescence compared with products of another set of probes.

Advantages are obtained when the probe target recognition relies on both hybridisation and enzymatic discrimination, so that the signal output is dependent on correct enzymatic probe reaction. Preferably, recognition of the target sequence by the probe comprises hybridisation of the probe to the target sequence and generation of a ligation product, where the generation of the ligation product is dependent on the specific hybridisation of the probe to its target sequence. Probes which are designed to be especially suitable for use in the present method are described herein. However, the probes are not limited to any one design of probe, and a variety of known nucleic acid probes may be conveniently used, including for example padlock probes, selector probes, oligonucleotide ligation probes, molecular inversion probes, and tandem probes.

A first aspect of the this disclosure provides a method of detecting a species of nucleic acid in a sample, comprising contacting the sample with a set of probes, wherein each probe specifically recognises a distinct target sequence within the species of nucleic acid to be detected, providing conditions under which the target sequences in the species of nucleic acid are at least partially single stranded, providing conditions for annealing and ligation, under which conditions the probes hybridise to their target sequences and generate ligation products, each ligation product comprising a ligation junction, and detecting a cumulative signal which is a combination of individual signals from all ligation products, wherein detection of the signal indicates the presence of the species of nucleic acid in the sample.

A second aspect of this disclosure provides a method is a method of quantifying a species of nucleic acid in a sample, comprising contacting the sample with a set of probes, wherein each probe specifically recognises a distinct target sequence within the species of nucleic acid to be quantified, providing conditions under which the target sequences in the species of nucleic acid are at least partially single stranded, providing conditions for annealing and ligation, under which conditions the probes hybridise to their target sequences and generate ligation products, each ligation product comprising a ligation junction, and detecting a cumulative signal which is a combination of individual signals from all ligation products, quantifying the cumulative signal to determine a signal level, wherein the signal level is proportional to the quantity of the species of nucleic acid in the sample, and thereby determining the quantity of the species of nucleic acid in the sample.

The method may be used to quantify a first species of nucleic acid relative to a second species of nucleic acid in a sample. Accordingly, the method may comprise contacting the sample with a first set of probes and a second set of probes, wherein the probes of the first set each specifically recognise a distinct target sequence within the first species of nucleic acid and wherein the probes of the second set each specifically recognise a distinct target sequence within the second species of nucleic acid, providing conditions under which the target sequences in the first and second species of nucleic acid are at least partially single stranded, providing conditions for annealing and ligation, under which conditions the probes hybridise to their target sequences and generate ligation products, each ligation product comprising a ligation junction, detecting a first cumulative signal which is a combination of individual signals from the ligation products generated by probes of the first set, and quantifying it to determine a first signal level, wherein the first signal level is proportional to the quantity of the first species of nucleic acid in the sample, detecting a second cumulative signal which is a combination of individual signals from the ligation products generated by probes of the second set, and quantifying it to determine a second signal level, wherein the second signal level is proportional to the quantity of the second species of nucleic acid in the sample, and comparing the first and second signal levels, thereby determining the relative quantities of the first and second nucleic acid species in the sample.

Another aspect provides a method of quantifying a first chromosome or chromosomal locus relative to a second chromosome or chromosomal locus in a sample, comprising contacting the sample with a first set of probes and a second set of probes, wherein the probes of the first set each specifically recognise a distinct target sequence within the first chromosome or chromosomal locus and wherein the probes of the second set each specifically recognise a distinct target sequence within the second chromosome or chromosomal locus, providing conditions under which the target sequences in the first and second chromosome or chromosomal locus are at least partially single stranded, providing conditions for annealing and ligation, under which conditions the probes hybridise to their target sequences and generate ligation products, each ligation product being a circle of nucleic acid comprising a ligation junction, providing conditions for rolling circle replication of the circles of nucleic acid, counting the number of first rolling circle replication products, wherein rolling circle replication products are amplified from the ligation products generated by probes of the first set to provide a first count, counting the number of second rolling circle replication products, wherein the second rolling circle replication products are amplified from the ligation products generated by probes of the second set to provide a second count, and comparing the first and second counts, thereby determining the relative quantities of the first and second nucleic acid species in the sample.

In these embodiments, the rolling circle amplification products may be individually counted by: (a) obtaining a substrate comprising a plurality of complexes distributed on the surface of the substrate, wherein each of the complexes comprises a single RCA product and a plurality of labelled oligonucleotide probes that are hybridized to the RCA product, wherein the complexes corresponding to the first rolling circle amplification products and the complexes corresponding to the second rolling circle amplification products are distinguishably labelled; and (b) counting the number first RCA products and, independently, counting the number of second RCA products, that are present in an area of the substrate. In this embodiment, the oligonucleotides may be fluorescently labelled.

Generally, the number of probes will be at least ten for each species of nucleic acid to be detected or quantified. The number of course refers to the number of different probes, rather than the absolute number of molecules of the probe.

Accordingly, the nucleic acid will contain at least ten different specific target sequences, and the cumulative signal is a combination of individual signals of at least ten unique probes, this cumulative signal representing the one species of nucleic acid. High levels of multiplex can be used to obtain correspondingly high levels of signal amplification. For example, at least 100, at least 1,000, at least 10,000 or even greater numbers of probes may be used for each species of nucleic acid to be detected or quantified.

As noted, a variety of probe designs are suitable for use in the present method. Probes that generate ligation products following correct hybridisation to their target sequences include:

a) Padlock probes, where the probe circularises by hybridising to the target sequence, and a circle of probe nucleic acid is generated by ligation. Padlock probes are described in U.S. Pat. No. 5,854,033 (Lizardi), WO99/49079 (Landegren) and U.S. Pat. No. 5,871,921 (Landegren & Kwiatkowski). A version of the padlock probe known as the inversion probe is described in U.S. Pat. No. 6,858,412 (Willis et al.). Inversion probes are padlock probes containing a cleavage site in the probe backbone, allowing the circularised probe to be cleaved to form a linear product, which may then be amplified and detected.

b) Tandem probes, which circularise together with a bridging oligonucleotide on binding to the target sequence. The target sequence templates ligation of two probe sequences with a bridging oligonucleotide between them. The two probe sequences are then ligated to form a circle. Probes of this type are described in US2013/0172212 (Ariosa). Tandem probes are similar to the padlock probes but circularise the probe in a separate step after ligation instead of during ligation.

c) Target circularising probes. In probes of this type, a target sequence fragment is circularised by a template oligonucleotide. Ends of the target sequence can be ligated together, optionally with an intervening sequence between them. Target circularising probes are described in WO2008/033442 (Stanford). EP1997909 (derived from WO99/49079) describes a probe having two adjacent sequences complementary to a defined 5' target sequence and a defined 3' target sequence, so that hybridisation of the target fragment to the probe brings the target ends together to template ligation of the target ends to circularise the target nucleic acid.

d) Selector probes, which are double stranded selector constructs having one or two protruding ends complementary to ends of the target sequence, which hybridise to the target sequence and are ligated to each end of the target sequence, forming a circular or linear ligation product containing probe nucleic acid and the target sequence. A variety of selector probes are known. Selectors are described for example in WO2005/111236 (Dahl); WO2011/009941 (Olink Genomics); WO2011/067378 (Olink Genomics) and WO2008/153492 (Agilent).

e) OLA (oligonucleotide ligation assay) probes. These probes have been described for use in SNP genotyping. Each probe comprises a pair of oligonucleotides which hybridise to adjacent regions of a target sequence so that a 5' end of one oligonucleotide anneals adjacent to a 3' end of the other nucleotide and the ends are then ligated. Versions of OLA probe approaches include upstream gap fill polymerisation (golden gate assay) or gap fill by ligation of an additional oligonucleotide in between the two flanking probes (DANSR assay). The golden gate assay was described in Fan, J. B. et al. Highly parallel SNP genotyping. Cold Spring Harb. Symp. Quant. Biol. 68, 69-78 (2003). The DANSR assay was described in A. B. Sparks, E. T. Wang, C. A. Struble et al, Selective analysis of cell-free DNA in maternal blood for evaluation of fetal trisomy, Prenat Diagn (2012).

In general, desirable probes for use in the present method are probes that hybridise to the target sequence and generate a ligation product, where the generation of the ligation product is dependent on the specific hybridisation of the probe to its target sequence. This includes all the example probes listed above. Preferably, the ligation product is a product of double ligation (e.g. selector probes and tandem probes). Preferably, the ligation product includes the target sequence itself—for example where the target sequence is a fragment of the nucleic acid species, the fragment itself is ligated to the probe and so incorporated into the ligation product. This allows the target sequence to be verified by sequencing the product. A ligation product may be circular or linear nucleic acid, but there are certain advantages with a circular product (e.g. using padlock probes, selector probes or target circularising probes) such as the ability to clonally amplify and detect the products of rolling circle replication.

In some cases, therefore, probes used in the present method will have one or more of the above features.

Described herein is a new design of probe which is ideal for use in the methods of the present method. The probes have an especially desirable combination of features, including (in various embodiments) all of the above attributes. These novel probes comprise a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively.

Under conditions for annealing and ligation, the head and tail sequences hybridise to the flanking sequences, and the target fragment, if present, hybridises to the target-complementary sequence, thereby positioning the ends of the target fragment in juxtaposition with the 5' end of the head sequence and the 3' end of the tail sequence. The 5' end of the head sequence and the 3' end of the target fragment hybridise to adjacent nucleotides of the targeting oligonucleotide, and the 3' end of the tail sequence and the 5' end of the target fragment hybridise to adjacent nucleotides of the targeting oligonucleotide. If the target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment.

The product of double ligation may be circular or linear, according to the specific probe design, which is elaborated elsewhere herein.

Provided herein is method of sample analysis. In certain embodiments, the method comprises: a) hybridizing a sample comprising fragmented DNA (e.g., a sample that has been digested by a restriction enzyme) with a probe mix comprising a first set of probes, wherein the probes of the first set of probes hybridize to different sites (i.e., different sequences) in a first chromosome and form non-covalently circular products containing ligatably adjacent junctions when hybridized to DNA fragments from the first chromosome. In this context, the term "ligatably adjacent" is intended to mean that there are no intervening nucleotides between two oligonucleotides and they can be ligated to one another using a ligase. Examples of such probes are described in greater detail above and below. Examples of such probes are illustrated by example in FIGS. 3 and 4. Next, as shown in FIG. 2, the method comprises: b) ligating the ligatably adjacent junctions together to produce a plurality of covalently circular ligation products. As such, the next step of the method comprises: c) amplifying the covalently circular ligation products by rolling circle amplification (RCA) to produce a plurality of RCA product molecules. The RCA products can then be labelled and quantified, thereby, thereby providing an estimate of the amount of DNA corresponding to the first chromosome in the sample. Circularlized products provide a significant advantage for detection because they can be amplified by rolling circle amplification (RCA). RCA produces hundreds or thousands of copies of a circularized product in a single molecule, thereby effectively amplifying the circularized product and making it relatively easy to detect them individually using, e.g., labelled oligonucleotides that hybridize to a motif in the product. Quantifying signals from individual RCA products is significant because, in many applications (e.g., non-invasive pre-natal diagnosis by analysis of cell free DNA), the number of fragments corresponding to particular chromosomes (e.g., chromosome 21) needs to be determined quite accurately and without bias. Typical analysis methods use PCR which, as is well known, is a very biased procedure in that some sequences are amplified much higher efficiencies than others. This makes PCR-based strategies impractical for many diagnostic efforts.

FIG. 8 illustrates how the rolling circle amplification products can be quantified. In this method, the quantifying step may be done by separating individual rolling circle amplification product molecules produced in step c) from one another, and counting the number of individual rolling circle amplification product molecules in a defined area or volume. As shown in FIG. 8, the circularized products 22 (composed circularized products 22a, 22b, 22c and 22d) that comprise target sequence X and flanking sequences A and B are amplified by primer 52 to produce a set of RCA products. The RCA products are then distributed on the surface, and the number of RCA products can be directly counted by microscopy, where the term "distributing" is intended to mean that the RCA products are deposited on the surface of a planar substrate, and allowed to spread out. The RCA products do not need to be bound to the substrate, but they can be in certain cases (e.g., via biotin or the like).

In these embodiments, the quantifying step may be done by: i. hybridizing a labelled oligonucleotide to the RCA product molecules, wherein the labelled oligonucleotide hybridizes to a sequence that is repeated in the RCA product, thereby producing a plurality of complexes that each comprise a single RCA product and a plurality of labelled oligonucleotides that are hybridized to the RCA product; and ii. counting the number of labelled complexes in a defined area on the surface of the substrate. As shown in FIG. 2, at the point of detection, an RCA product is part of a complex containing the RCA product itself, a single circularized product, and a plurality of labelled oligonucleotides that hybridize to a sequence that is repeated in the RCA product.

As would be recognized, the RCA products can be labelled before or after they are distributed on the substrate. As such, in these embodiments, the quantifying step may be done by: (a) obtaining a substrate comprising the labeled complexes distributed on the surface of the substrate; and (b) counting the number of RCA products that are present in the first area of the substrate. The method may be multiplexed so that other cyclic products can be quantified at the same time. For example, the sets of probes used in the method may contain distinguishable sequence (for example, chromosome 21 probes may contain a first sequence and chromosome 18 probes may contain a second sequence), and the different sets of RCA products made as a result of circularization of those probes can be distinguished using distinguishably labelled oligonucleotides that hybridize to the first and second sequences.

In these embodiments, the method may comprise: (a) obtaining a substrate comprising a first and second pluralities of complexes distributed on the surface of the substrate, wherein each of the complexes comprises a single RCA product and a plurality of labelled oligonucleotide probes that are hybridized to the RCA product, the first and second pluralities of complexes are distinguishably labelled, and the first and second pluralities of complexes correspond to different chromosomes; and (b) counting the number of the first plurality of RCA products and, independently, counting the number of the second plurality of RCA products, that are present in the first area of the substrate. In this embodiment, the oligonucleotides may be fluorescently labeled. Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002).

In some embodiments, the sample may contain fragments of genomic DNA, e.g., genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, where in certain embodiments the mammal is a human. In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cell-free DNA obtained from blood, e.g., from the blood of a pregnant female. In certain embodiments, the genomic DNA may be amplified, e.g., using a whole genome amplification method, prior to fragmentation. The sample may contain microbial DNA, e.g., DNA from the genome of a virus or bacteria.

In any embodiment, the probe mix may comprises a second set of probes, wherein the probes of the second set of probes hybridize to different sites in a second chromosome and form non-covalently circular products containing ligatably adjacent junctions when hybridized to DNA fragments from the second chromosome. In this method, the quantifying step may comprise separately quantifying the number of rolling circle amplification product molecules that correspond to the first and second chromosomes, thereby providing an estimate of the relative amount of DNA corresponding to the first and second chromosomes in the sample. As noted above, the RCA products corresponding to the first and second chromosomes can be separately quantified by hybridizing distinguishably labelled oligonucleotides to them and distributing them on the surface of a support, e.g., a microscope slide.

The method may be used to examine sub-chromosomal regions, too. In these embodiments, the first set of probes may hybridize to different sites in a first region of a chromosome. In these embodiments, the probe mix may comprises a second set of probes, wherein the probes of the second set of probes hybridize to different sites in a second region in the first chromosome and form non-covalently circular products containing ligatably adjacent junctions when hybridized to DNA fragments from the second chromosome. In this method, the quantifying step may comprise comprise separately quantifying the number of rolling circle amplification product molecules that correspond to the first and second regions of the first chromosomes, thereby providing an estimate of the relative amount of DNA corresponding to the first and second regions of a chromosome in the sample. As noted above, the RCA products corresponding to the first and second chromosomes can be separately quantified by hybridizing distinguishably labelled oligonucleotides to them and distributing them on the surface of a support, e.g., a microscope slide.

For non-invasive pre-natal testing embodiments, the target fragment may be from human chromosome 21, 13 or 18, for example, although other chromosomal abnormalities (e.g., other trisomies, or deletions or insertions of a particular region) can be examined. Copy-number variations are alterations of genomic DNA that correspond to relatively large regions of the genome that have been deleted or amplified on certain chromosomes. CNVs can be caused by genomic rearrangements such as deletions, duplications, inversions, and translocations. Copy number variation has been associated with various forms of cancer (Cappuzzo F, Hirsch, et al. (2005) 97 (9): 643-655) neurological disorders (Sebat, J., et al. (2007) Science 316 (5823): 445-9, including autism (Sebat, J., et al. (2007) Science 316 (5823): 445-9), and schizophrenia St Clair D (2008). Schizophr Bull 35 (1): 9-12. Detection of copy number variants of a chromosome of interest or a portion thereof in a specific cell population can be a powerful tool to identify genetic diagnostic or prognostic indicators of a disease or disorder. In some embodiments, the first chromosome is chromosome 21 and the second chromosome is selected from chromosome 13 and chromosome 18.

In any embodiment, each of the non-covalently circular products comprises a fragment of DNA from the sample. In the implementations shown in FIGS. 3 and 4, the probes used in the method may comprise: i. a head sequence and a tail sequence, wherein the head and tail sequences are at the ends of a first oligonucleotide molecule; and ii. a splint sequence comprising, in order: an upstream flanking sequence that is complementary to the head sequence; a target complementary sequence that is complementary to a target fragment; and a downstream flanking sequence that is complementary to the tail sequence. In these embodiments, in the non-covalently circular products, the ends of the target fragment are ligatably adjacent to the ends of the head and tail sequences in the first oligonucleotide molecule. In these embodiments, the splint sequence may be in the first oligonucleotide molecule. Alternatively, the splint sequence may be in a second oligonucleotide molecule.

In some embodiments, the method comprises hybridizing the sample with a set of at least 50 (e.g., at least 100, at least 200, at least 500, at least 1,000, at least 2,000 or at least 5,000) of said probes, wherein said probes target different fragments on the same chromosome (e.g., human chromosome 21, 13 or 18), and wherein the method results in a plurality of cyclic products that comprises the target fragments. The number of cyclic products produced can be quantified by, e.g., amplifying them using RCA and counting the number of RCA products, as described above.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

Multiplex Recognition of Target Sequences

Figure 1:
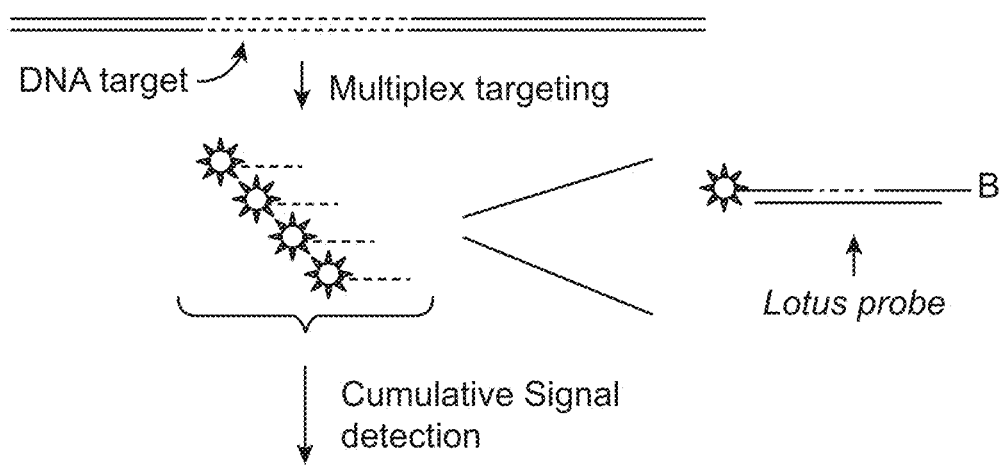
FIG. 1 schematically illustrates one embodiment of the subject method in which a DNA target species of interest is contacted with multiple labelled linear probes and the cumulative signal from the bound labels is detected.
Figure 2:
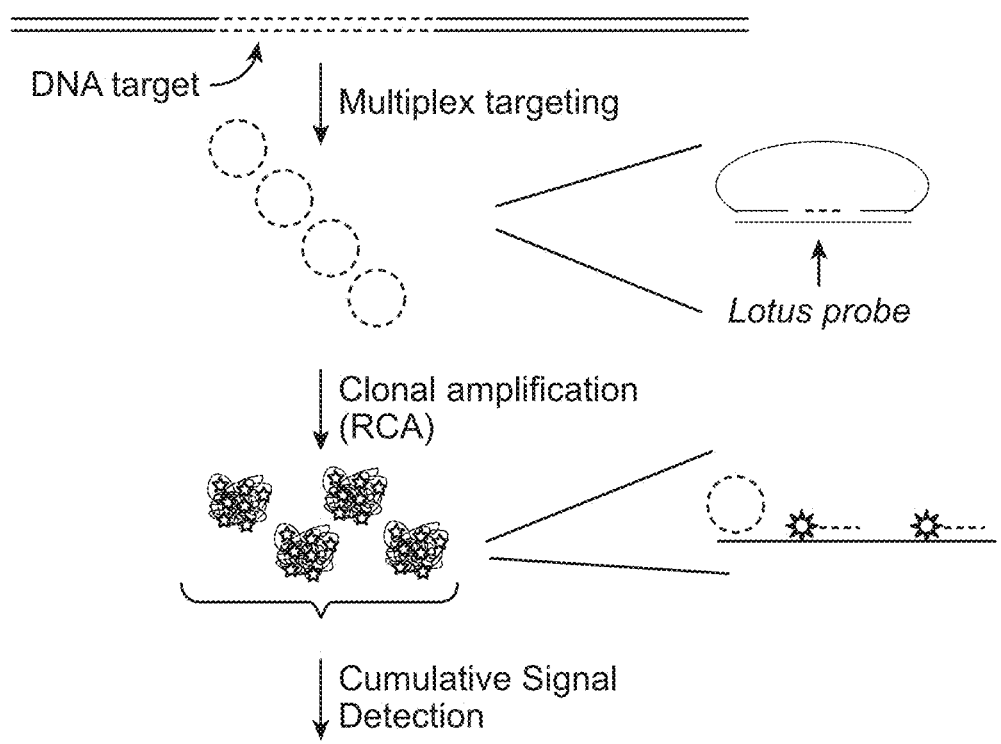
FIG. 2 schematically illustrates one embodiment of the subject method in which a DNA target species of interest is contacted with multiple circularising probes which are clonally amplified by rolling circle amplification and the cumulative signal of the amplified products is detected.

The species of nucleic acid to be detected or quantified includes multiple target sequences. These target sequences are distinct from one another. They will therefore represent spatially distinct locations on the nucleic acid, although they may be overlapping. Target sequences within a given species of nucleic acid may be overlapping, non-overlapping, or a there may be a mixture of overlapping and non-overlapping target sequences. Preferably the target sequences are non-overlapping. Effectively, the set of target sequences for a species of nucleic acid represent different epitopes for detection of the same species of nucleic acid.

Usually there will be at least 10, at least 100, at least 1,000 or at least 10,000 distinct target sequences in the nucleic acid, and each of these may be probed.

Suitable concentrations of probes may be determined based on the concentration (or expected concentration) of the species of nucleic acid in the sample. As illustrated in the Examples, probes may be added to the sample at a concentration of 10 pM per probe. Where a sample is contacted with multiple probes (e.g. a set of probes), concentrations of the individual probes may be 10 pM. Preferably, probes are used in excess of the expected concentration of the nucleic acid species of interest to be detected or quantified. Use of excess probe should ensure that all copies of target sequences present in the sample are recognised. This maximises the sensitivity of detection. Also, where methods involve quantification, it ensures that the detection of the ligation products or cumulative signal from a set of probes is proportional to the quantity of target sequences in the sample.

Where one species of nucleic acid is to be quantified relative to another, the target sequences are specific to the species of nucleic acid, i.e., not found in the other species of nucleic acid, and preferably not found in any other species of nucleic acid that may be in the sample.

For many diagnostic and other applications, the species of nucleic acid is a chromosome or chromosomal locus, e.g., a human chromosome or chromosomal locus. Each target sequence fragment may thus be specific to that one chromosome of an organism's genome. In other words, it may be found only in one chromosome of the genome and not in other chromosomes of that genome. Commonly, the present method will be used for analysis of the human genome, in which case the target sequence may be a fragment specific to one human chromosome, i.e., found in that chromosome and not in other human chromosomes. For example, target sequences may be specific to chromosome 21. The target sequences may be specific to one locus of a chromosome. Accordingly, they may be found in that chromosomal locus and not in other loci of the same chromosome or other chromosomes of the same genome. For example, the target sequences may be specific to one locus of a human chromosome.

A given species of nucleic acid in a sample may encompass some variability, for example a sample may comprise chromosomes of different individuals, such as nucleic acid obtained from maternal blood which contains maternal DNA and foetal DNA. Here the species of interest may be a particular chromosome, but it is convenient to detect all copies of that chromosome whether of foetal or maternal origin. Thus, a species of interest may be one chromosome or chromosomal locus, and the target sequences are found in that chromosome or locus in both maternal and foetal copies of the chromosome or chromosomal locus.

The species of nucleic acid may be fragmented. The target sequences may be sequences of fragments of the species of nucleic acid, i.e., target fragments.

Preferably, the target sequences are fragments whose sequence is pre-defined. The sequence of the entire fragment including the ends may be known. Known fragments of pre-defined sequence can be produced by specific, rather than random, fragmentation of the species of nucleic acid. Specific fragmentation methods include digestion with restriction enzymes, PCR (e.g., multiplex PCR), and other methods of sequence directed fragment end definition, including other enzymes, ribozymes, or a combination of such techniques.

A preferred method of fragmentation is digestion with a restriction endonuclease or a combination of two or more restriction endonucleases. Thus, the sample may be a restriction enzyme digest of nucleic acid and the target sequences may be restriction fragments.

A variety of specific nucleic acid cleaving enzymes are known and any suitable enzyme may be used in the present method, including enzymes which cleave at a pre-defined position within a specific nucleic acid sequence, or endonucleolytic enzymes which cleave either after or before a specific nucleic acid recognition sequence and nicking enzymes (side-cutting enzymes). Catalytic nucleic acids, such as ribozymes, can be used as well for DNA fragmentation. The enzymes may cleave double stranded nucleic acid to produce a blunt end or a sticky end, or may cleave a single strand of nucleic acid. Various types of restriction enzymes are known, including Type I, Type II, Type III, Type IV and Type V. Suitable enzymes or combinations of enzymes can be selected for use in the present method as desired. For example, nucleic acid in a sample (e.g. 10 ng of DNA) may be digested with restriction enzyme (e.g. 1 U) in corresponding compatible restriction enzyme buffer. The reaction may be incubated under suitable conditions (e.g. 37° C. for 1 hour), followed by enzymatic deactivation (e.g. at 80° C. for 20 minutes).

Another convenient method of providing fragmented nucleic acid is to use primers for amplification of specific linear sequences from the species of nucleic acid. Multiplex PCR can be used, treating the nucleic acid with multiple specific primer pairs to amplify multiple specific fragments. In this case, the ends of the target sequences correspond to the sequences of the pair of primers.

Samples of nucleic acid may be provided in any suitable way, for example as samples of biological tissue or fluid from patients. Samples may be blood samples, whole blood, plasma, or serum, tissue samples, e.g., formalin fixed paraffin embedded samples of tissue, or may be samples of nucleic acid extracted from blood or tissue.

The sample may be any sample that contains nucleic acid. The nucleic acid contained in the sample may be DNA and/or RNA. The sample may be complex, e.g. whole genomic DNA, or cDNA from a whole organism, tissue or cell population, or a fraction thereof. In this regard it may, for example, be a direct product of a nucleic acid isolation procedure, or of a cell lysis procedure, or it may be further be fractionated or purified in some way, e.g. it may contain nucleic acids which have been partially or fully separated in some way, or treated in any way, e.g. RNA to produce cDNA. The sample may be from any eukaryotic or prokaryotic or viral source, e.g. may be microbial (for example bacterial or fungal), plant, or animal. Thus, for example, the species of nucleic acid to be detected or quantified may be microbial DNA. Preferably the sample is of human origin, e.g., human genomic DNA. The sample may be a tissue or blood sample from an animal, where the nucleic acid to be detected is microbial, e.g., bacterial, viral or fungal. For many diagnostic and other applications, the sample is a sample of fragmented chromosomes (e.g., human chromosomes or microbial chromosomes). For methods relating to non-invasive prenatal diagnostics, the sample is derived from the blood of a pregnant woman and comprises foetal DNA. In other examples, the nucleic acid to be detected or quantified is tumour associated DNA.

A given species of nucleic acid in a sample may encompass some variability, for example a sample may comprise chromosomes of different individuals, such as nucleic acid obtained from maternal blood which contains maternal DNA and foetal DNA. Here the species of interest may be a particular chromosome, but it is convenient to detect all copies of that chromosome whether of foetal or maternal origin. Thus, a species of interest may be one chromosome or chromosomal locus, and the target fragments are obtained from that chromosome or locus in both maternal and foetal copies of the chromosome or chromosomal locus.

The present method may be performed on the samples in vitro. Accordingly, the methods generally do not include diagnosis carried out in vivo on the human or animal body or methods of treatment of the human or animal body by surgery or therapy. Nevertheless, the results of the in vitro diagnostic methods may be used to inform the subsequent treatment of patients.

Denaturing the Target Nucleic Acid

The probe recognises and binds the target sequence in at least partially single stranded form, through hybridisation. For some designs of probe the target sequence should be fully single stranded, particularly those which hybridise to the full length of the target sequence. For other probes, e.g., those which hybridise to only regions of the target sequence, only partially single stranded target nucleic acid is required. Accordingly, suitable conditions should be provided to expose the binding site of the target sequence to the probe, depending on the type of probe employed.

If the target sequence in the sample is not already single stranded or at least partially single stranded, conditions should be provided to separate the single stranded target sequence from its complementary nucleic acid strand. Such conditions may be denaturing conditions or, in some cases, treatment with exonuclease.

The denaturing conditions may be a sufficiently high temperature to separate the target sequence from its complementary sequence. Denaturing conditions may be incubation at 95° C. for a suitable time, e.g. 10 minutes. Alternatively chemical denaturation may be performed.

Complementarity and Hybridisation

Specific binding between the probe and its target sequence is an important feature of the methods of the present method. A probe preferably comprises a single target complementary sequence which recognises the target sequence. However, as illustrated by padlock probes and selector probes for example, probes may comprise multiple sequences complementary to different regions of a target sequence.

Maximum specificity for the target sequence is achieved if the probe comprises a target complementary sequence which is the exact complement of the target sequence or region of the target sequence, so that there is perfect hybridisation between the probe and the target sequence. However, this is not essential in all cases, and a small degree of mismatching may be accepted, for example to allow detection of sequences which exhibit allelic variation where it is desired to detect the target sequence regardless of the exact allele present in the sample. Alternatively, multiple probes can be designed for variant sequences. This can enable both detection and discrimination of different alleles or mutations. It is envisaged that the majority of probes will have perfect complementarity for their target sequences but some probes may bind targets with minor mismatches.

In some embodiments, the probes used in the present method each comprise a target complementary sequence having fewer than 5 base pair mismatches with the target sequence or region of target sequence. There may optionally be one, two, three or four base pair mismatches between the target sequence or region and the target complementary sequence. A mismatch may be a point at which a corresponding base is absent from one sequence, so that the complementary sequence forms a loop at the mismatched point, or may occur where a non-complementary nucleotide is present in one sequence and so does not pair with the base at the corresponding position of the other sequence. Where there is an incorrect base pairing, i.e., a pairing of A or T with C or G, hydrogen bonding does not take place between the bases of the two strands, although hybridisation will still take place between the target sequence and the target complementary sequence of the targeting oligonucleotide due to base-pairing between the nucleotides neighbouring the mismatch. Mismatches may be wobble bases. A wobble base would normally correspond to a position in the target complementary sequence that pairs with a position of known genetic variation in the target fragment. The probe may be synthesised by adding one or several dideoxynucleotides during the specific synthesis cycle for the wobble base position. This is typically the case for traditional oligonucleotide synthesis. Alternatively multiple separate probes may be produced, one for each genetic variant. This is typically the case if probes are synthesised using microarray based synthesis. A wobble base may correspond to single nucleotide differences between codons, where the different codons encode the same amino acid.

In general, longer target complementary sequences for hybridising longer target sequences or regions thereof may tolerate a higher number of mismatches compared with shorter target complementary sequences. The target complementary sequence may, for example, have at most 1 in 8, 1 in 9 or 1 in 10 base pair mismatches with the target sequence or region thereof. Any such mismatches should be restricted to the internal region of the target complementary sequence and target sequence or region, so that they do not inhibit ligation or sequence specific target fragmentation by e.g. restriction enzyme digestion. Accordingly, preferably there is perfect complementarity between the target sequence and the target complementary sequence in the terminal 6 to 8 nucleotides, preferably the terminal 10 nucleotides at each end of the target sequence.

Preferably, a probe comprises a single target complementary sequence which is the same length as the target sequence. The full length of the target sequence is thus bound by the target complementary sequence. Hybridisation of the target sequence to the targeting oligonucleotide represents a single binding event between the two nucleic acid molecules, contrasting with probes which bind the two ends of a target molecule or to two non-adjacent regions of the target.

The target complementary sequence may have a length of at least 10 nucleotides, for example at least 15 nucleotides. It may be up to 20, 25, 30, 35 or 40 nucleotides long. Preferred ranges include 10-20 nucleotides, 10-30 nucleotides, and 10-40 nucleotides. Such relatively short target complementary sequences are suitable for binding correspondingly short target sequences. The short sequence contributes to the specificity of the double ligation reaction, since DNA ligase is sensitive to base pair mismatches and will preferentially ligate perfectly matched sequences. Where mismatches are present in the footprint of DNA ligase bound to the double stranded sequence, the sequences may not be ligated, which provides an additional proofreading step ensuring high specificity in detecting the target sequence in preference to sequences of different but similar sequence. DNA ligase typically has a footprint of 6 to 8 bases on each side of the nick. Therefore, if the target sequence is 20 bases, 12 to 16 of the bases will be covered by ligase specificity.

The probe hybridisation will discriminate against mismatches especially in the central part of the hybridised sequence while the ligation will discriminate against mismatches at the ends of the target. Together this generates a highly specific detection.

As described in more detail elsewhere herein, a probe preferably comprises:

a targeting oligonucleotide which is longer than the target sequence and contains an internal target complementary sequence, so that hybridisation between the targeting oligonucleotide and the target sequence forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively.

These probes are particularly suitable for use where the species of nucleic acid is fragmented and the target sequences are fragments of defined sequence. The targeting oligonucleotide is longer than the target sequence since it includes the flanking sequences as well as the target complementary sequence. The upstream flanking region is upstream of or 5' of the target complementary sequence in the targeting oligonucleotide. The downstream flanking region is downstream of or 3' of the target complementary sequence in the targeting oligonucleotide. Accordingly, the target complementary sequence is internal to the targeting oligonucleotide and does not include an end of the targeting oligonucleotide, since it is flanked by the upstream and downstream flanking sequences.

The double stranded sequence produced by hybridisation of the target sequence and the target-complementary sequence may be considered a hybrid double stranded sequence, since it is a hybrid of the target and the probe. Typically the double stranded sequence adopts a double helical conformation, in which the target sequence is one strand and the targeting oligonucleotide is the other strand of the double helix. The hybrid double stranded sequence is flanked by the upstream and downstream flanking sequences of the targeting oligonucleotide, which in turn hybridise to the head and tail sequences to produce double stranded sequences. Again, these typically adopt the normal double helical conformation of double stranded nucleic acid.

The upstream and downstream flanking sequences are preferably different from each other, i.e., preferably have different sequences. It is preferred that the head sequence is complementary to the upstream flanking sequence but not to the downstream flanking sequence, and that the tail sequence is complementary to the downstream flanking sequence but not to the upstream flanking sequence. This ensures that the head and tail sequences hybridise only to the upstream and downstream flanking sequences respectively.

The head sequence will usually be the same length as the upstream flanking sequence. The tail sequence will usually be the same length as the downstream flanking sequence.

Normal lengths for the flanking sequences are between 10 and 40 nucleotides, for example 10-20 or 10-30 nucleotides. The flanking sequences may be the same length as each other. One or both flanking sequences may be the same length as the target-complementary sequence. The upstream and/or downstream flanking sequence may thus have a length of at least 10 nucleotides, for example at least 15 nucleotides. It may be up to 20, 25, 30, 35 or 40 nucleotides long.

Preferably, the head sequence is the complement of the upstream sequence. Preferably, the tail sequence is the complement of the downstream sequence. Perfect matching of the sequences is desirable for optimum binding of the probe so that the head and tail sequences are correctly positioned for ligation to the target sequence. Optionally, however, there may be one, two three or four base pair mismatches between the head sequence and the upstream flanking sequence, and/or between the tail sequence and the downstream flanking sequence. Preferably, there are fewer than 5 base pair mismatches.

Other than the target complementary sequence, probes should usually not be complementary to the target sequence or to other nucleic acids that may be present in the sample. This is to avoid unwanted hybridisation of the probe to nucleic acid other than the target. Thus, if the probe is for binding a sequence of human genomic DNA, the probe may be designed so that sequences other than the target complementary sequence are not complementary to human genomic DNA, so that the probe only hybridises to the target sequence and not to other nucleic acid in the sample.

Probes may include one or more custom sequences. A custom sequence is not complementary to other regions of the probe or to the target sequence—in other words it does not hybridise to other regions of the probe (outside the custom sequence) or to the target sequence under annealing conditions. The custom sequences may be used for detection, e.g. as barcodes or labels to identify probes belonging to a set, as described elsewhere herein.

Generation of Ligation Products

Under conditions for annealing and ligation, probes hybridise to their target sequences and are ligated to generate ligation products. Hybridisation of each probe results in generation of a ligation product. Accordingly, generation of the ligation product is dependent on the specific hybridisation of the probe to its target sequence.

The ligation product may comprise or consist of probe nucleic acid or target nucleic acid, or may comprise both probe and target nucleic acid. The ligation product comprises a ligation junction which is formed by the ligation of a 5' end of nucleic acid to a 3' end of nucleic acid. Where multiple nucleic acids are ligated together, there may be two ligation junctions.

The type of ligation product which is formed depends on the type of probe used. Ligation products may be are circles of nucleic acid or may be linear nucleic acid molecules.

An example of a probe which forms circular ligation product is the padlock probe. Various types of padlock probe are known, e.g. standard, gapfill, molecular inversion probes (MIP). Padlock probes are linear oligonucleotides with target complementary sequences at the ends and a non-target complementary sequence in between. Under the conditions for annealing and ligation, the target complementary sequences are brought together head to tail to hybridise to adjacent regions of the target sequence and are ligated form a circle of nucleic acid. Thus, the probe circularises by hybridising to the target sequence, and the ligation product is a circle of probe nucleic acid. The circular ligation product typically contains one ligation junction where the 5' and 3' ends of the linear probe are ligated together. Variations including bridging oligonucleotides and gap-fill probes are known. The probes may contain a cleavage site in the probe backbone, allowing the circularised ligation product to be cleaved to form a linear product, which may then be amplified and detected (MIPs).

Preferably, hybridisation of the probe to the target sequence positions an oligonucleotide of the probe for ligation to the target sequence. Accordingly, the target sequence may be incorporated into the ligation product. This is an advantage over probes such as padlock probes since it allows the target sequences to be verified by sequencing the ligation products. Preferably, the probe is ligated to each end of its target sequence, forming a ligation junction at each end of the target sequence. In such methods, the species of nucleic acid to be detected or quantified will preferably be fragmented to produce target fragments corresponding to the target sequences. Ends of the target fragment can then be ligated to ends of the probe, capturing the target sequence within the ligation product. In such cases, the target fragment is ligated in a highly specific reaction at both ends. Since the target fragment is typically the product of a specific fragmentation of nucleic acid, these ends will usually have a specific, pre-determined sequence. In the ligation step, these ends are specifically detected by sequence-dependent ligation to the head and tail sequences respectively. Preferably, binding of the target fragment to the probe creates two perfectly matched ligatable junctions, one between the 3' end of the target fragment and the 5' end of the head sequence and one between the 5' end of the target fragment and the 3' end of the tail sequence.

Ligation of a 5' end of nucleic acid to a 3' end of nucleic acid can occur when the two ends are base paired to adjacent nucleotides of a complementary sequence. Base pairing of the respective end nucleotides to the adjacent nucleotides forms a nucleic acid strand containing a nick between the two ends. Ligation of the two ends can be catalysed by DNA ligase. Providing conditions for ligation will therefore usually comprise providing a DNA ligase enzyme and reaction conditions under which the DNA ligase ligates the two ends to form a continuous nucleic acid strand, closing the nick. A number of ligase enzymes are commercially available, such as Ampligase (Epicentre), for which suitable conditions are to add 1 U enzyme and incubate at 55° C. for 1 hour in ligase buffer.

An examples of a probe which generates a ligation product incorporating the target sequence is the selector probe. These probes are double stranded selector constructs having one or two protruding ends complementary to ends of the target sequence, which hybridise to the target sequence and are ligated to each end of the target sequence, forming a circular or linear ligation product containing probe nucleic acid and the target sequence. Under the conditions for annealing and ligation, the end sequences of the selectors hybridise to the end sequences of the fragments and are ligated to the selectors. Where a probe comprises a pair of selector constructs each having a protruding end, each may be ligated to one end of a target fragment so that the ligation product is a linear nucleic acid comprising the target sequence between two probe sequences. Where a probe comprises a single selector construct having two protruding ends, it may be ligated to each end of the target fragment so that the ligation product is a circular nucleic acid comprising the target sequence and probe nucleic acid. In both cases, the ligation product includes two ligation junctions.

Numerous other examples of suitable probes are described elsewhere herein.

In some embodiments, the present method may use probes which comprise:

a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, wherein under the conditions for annealing and ligation, the head and tail sequences hybridise to the flanking sequences, and the target fragment, if present, hybridises to the target-complementary sequence, thereby positioning the ends of the target fragment in juxtaposition with the 5' end of the head sequence and the 3' end of the tail sequence, wherein the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment.

In these probes, the targeting oligonucleotide templates the target fragment for ligation to the head and tail sequences, due to the location of the target-complementary sequence between the flanking sequences. Under annealing conditions in the presence of the target fragment, the head and tail sequences hybridise to the flanking sequences, defining a gap between the 5' end of the head sequence and the 3' end of the tail sequence. The target fragment hybridises to the target-complementary sequence in the gap. Thus, hybridisation of the head and tail sequences and the target fragment to the targeting oligonucleotide positions the 3' end of the target fragment in juxtaposition with the 5' end of the head sequence, and positions the 5' end of the target fragment in juxtaposition with the 3' end of the tail sequence.

Positioning of two ends in juxtaposition provides a substrate for DNA ligase to ligate the ends together. It is preferable that the 5' end of the head sequence and the 3' end of the target fragment hybridise to adjacent nucleotides of the targeting oligonucleotide, and the 3' end of the tail sequence and the 5' end of the target fragment hybridise to adjacent nucleotides of the targeting oligonucleotide. Accordingly, the upstream flanking sequence may be immediately adjacent to the target-complementary sequence, with no intervening nucleotides. Similarly, the downstream flanking sequence may be immediately adjacent to the target-complementary sequence, with no intervening nucleotides. Adjacent 3' and 5' ends can be directly ligated by DNA ligase sealing the nick between them to form a continuous nucleic acid strand.

The product of the double ligation, i.e., the product of ligating both the head sequence and the tail sequence to the target fragment, is a continuous strand of nucleic acid. It is continuous in the sense that it contains no nicks or gaps, so all nucleotides in the strand are covalently joined.

The probe may be designed so that the continuous strand of nucleic acid comprising the head and tail sequences and the target fragment is a circle of nucleic acid. The term circle here refers to the topology of the strand being a closed loop, with no free end.

Under annealing conditions in the presence of the target fragment, the head and tail sequences hybridise to the flanking sequences, defining a gap between the 5' end of the head sequence and the 3' end of the tail sequence. The target fragment hybridises to the target-complementary sequence in the gap, thereby positioning the ends of the target fragment in juxtaposition with the 5' end of the head sequence and the 3' end of the tail sequences, and completing a circle of nucleic acid which comprises the target fragment and the head and tail sequences.

The nucleic acid molecules which form the circle have their ends in juxtaposition. Ligation of the ends produces the continuous circular strand of nucleic acid comprising at least the head and tail sequences and the target fragment.

Figure 3:
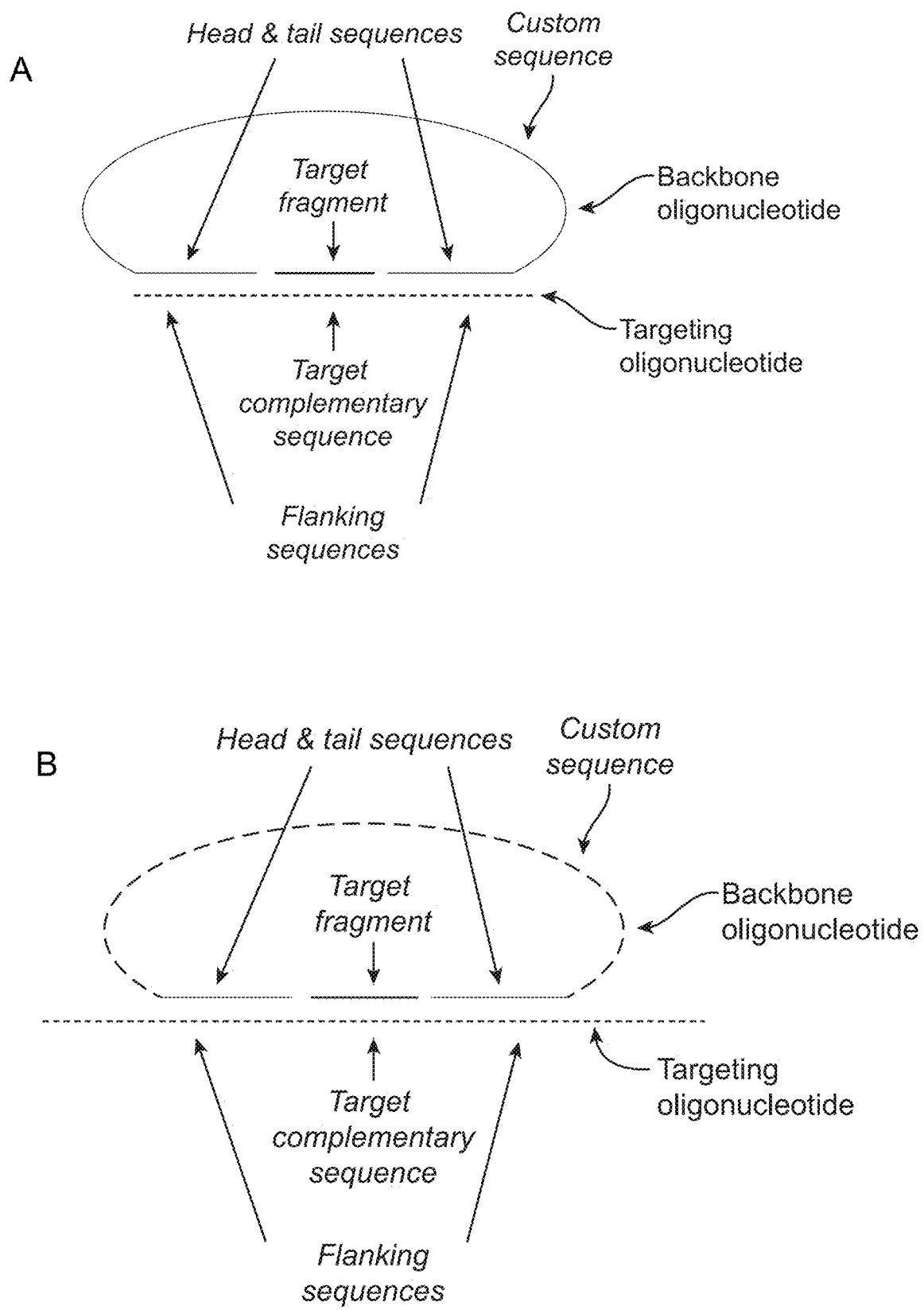
FIG. 3 shows a probe comprising a circularised backbone oligonucleotide bound to its target fragment. The probe is illustrated in two versions, A and B.

Probes which form a circle of nucleic acid include probes in which the head and tail sequences are provided on a single nucleic acid molecule. For example, in addition to the targeting oligonucleotide the probe may comprise a backbone oligonucleotide having the head and tail sequences at its 5' end 3' ends respectively, wherein the head and tail sequences of the backbone oligonucleotide bind in trans to the flanking sequences of the targeting oligonucleotide under the annealing conditions. The backbone oligonucleotide may comprise a custom sequence between the head and tail sequences. FIG. 3 illustrates embodiments of such probes. Alternatively, the head and tail sequences of the backbone oligonucleotide may be adjacent, with no custom sequence between them.

Figure 4:
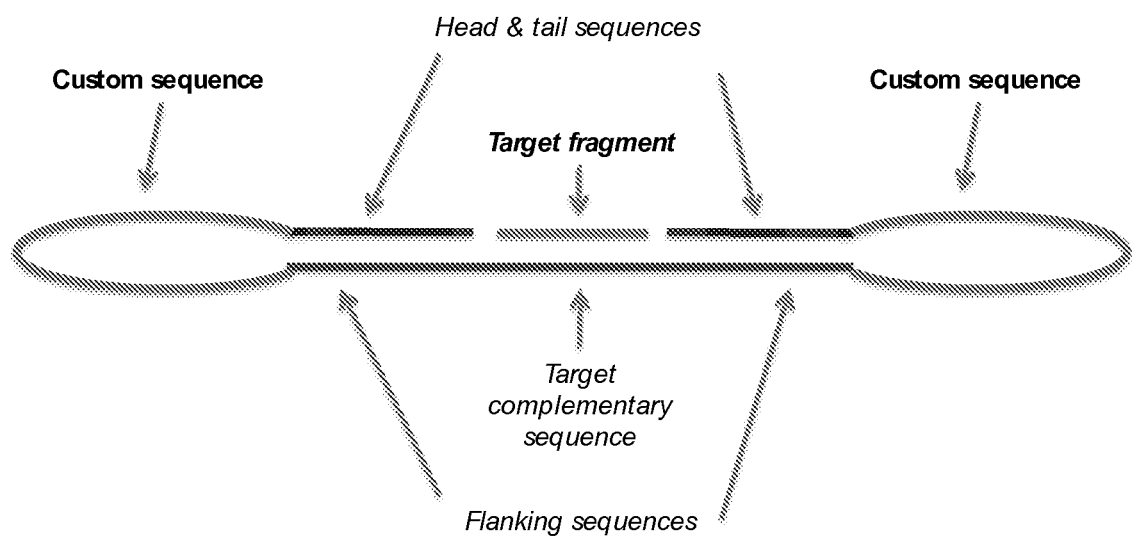
FIG. 4 shows a circularised single oligonucleotide probe with bound target fragment.

In another example, the head and tail sequences may be at ends of the targeting oligonucleotide and bind in cis to the flanking sequences under the annealing conditions. The targeting oligonucleotide may comprise a custom sequence between the targeting oligonucleotide and the head and/or tail sequence. FIG. 4 illustrates an embodiment of such a probe.

Figure 5:
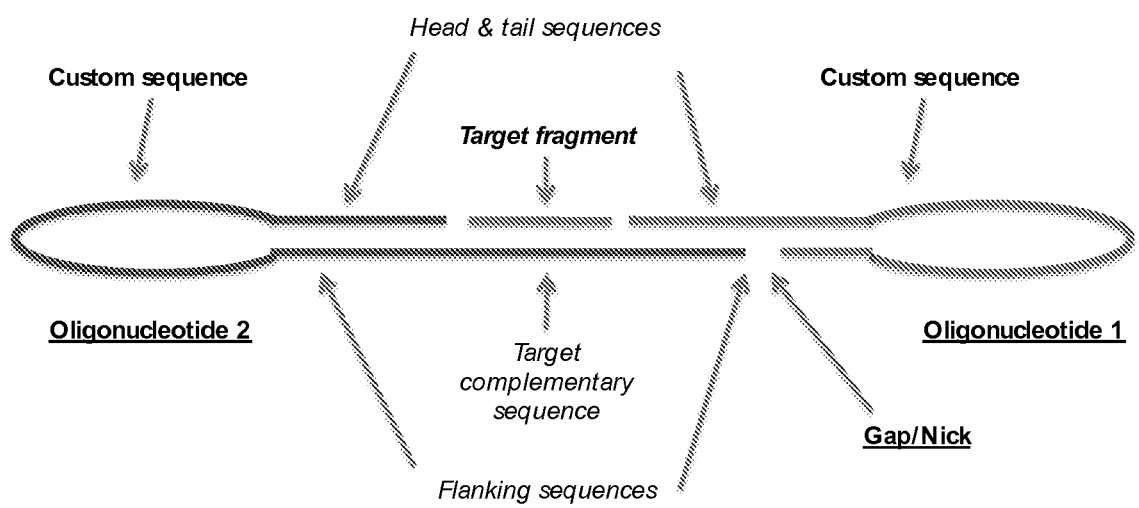
FIG. 5 shows a circularised double looped probe composed of a targeting oligonucleotide and a looped backbone oligonucleotide, with bound target fragment.

Probes which form a circle of nucleic acid also include probes in which the head and tail sequences are provided on different nucleic acid molecules. In such cases, the circle of nucleic acid which forms under the annealing conditions will comprise at least three nucleic acid molecules—the target fragment, the head sequence and the tail sequence. The ends of the nucleic acid molecules will all be in juxtaposition, as previously noted. More than two ligation reactions are required to form the continuous circular strand of nucleic acid in such cases. An example is where the tail sequence is the 3' end of the targeting oligonucleotide, and the probe comprises a backbone oligonucleotide having the head sequence at its 5' end. Under the annealing conditions the tail sequence binds in cis to the downstream flanking sequence of the targeting oligonucleotide, and the head sequence of the backbone oligonucleotide binds in trans to the upstream flanking sequence of the targeting oligonucleotide. Binding in cis means that the binding takes place on the same nucleic acid molecule, i.e., a single strand of nucleic acid forms a three dimensional structure in which different regions are brought together and hybridise. Binding in trans means that the binding takes place between different nucleic acid molecules. Optionally, the backbone oligonucleotide comprises a pair of inverted repeat sequences which form a hairpin structure under annealing conditions, thereby positioning the 3' end of the backbone oligonucleotide in juxtaposition with the 5' end of the targeting oligonucleotide. There is a nick between the two ends. A probe of this type is illustrated in FIG. 5. When conditions for ligation are provided, the 5' end of the targeting oligonucleotide is ligated to the 3' end of the backbone oligonucleotide. The product of double ligation is a circle of nucleic acid comprising the targeting oligonucleotide, the target fragment and the backbone oligonucleotide. Alternatively, where there is a gap between the 5' end of the targeting oligonucleotide and the 3' end of the backbone oligonucleotide, the probe shown in FIG. 5 will not be circularised by ligation—instead the continuous strand of nucleic acid comprising the head and tail sequences and the target fragment is a linear strand of nucleic acid.

The probe may alternatively be arranged in the opposite orientation so that the head sequence is at the 5' end of the targeting oligonucleotide and the probe comprises a backbone oligonucleotide having the tail sequence at its 3' end. In this case, under the annealing conditions the head sequence binds in cis to the upstream flanking sequence of the targeting oligonucleotide, and the tail sequence of the backbone oligonucleotide binds in trans to the downstream flanking sequence of the targeting oligonucleotide. Again, the backbone oligonucleotide may comprise a pair of inverted repeat sequences which form a hairpin structure under annealing conditions to position the 5' end of the backbone oligonucleotide in juxtaposition with the 3' end of the targeting oligonucleotide. The 3' end of the targeting oligonucleotide is then ligated to the 5' end of the backbone oligonucleotide so that the product of double ligation is a circle of nucleic acid comprising the targeting oligonucleotide, the target fragment and the backbone oligonucleotide. Alternatively, as noted above, the annealing may position the 5' end of the backbone oligonucleotide near the 3' end of the targeting oligonucleotide but separated by a gap of one or more nucleotides. The ligated product will then be a continuous linear strand of nucleic acid comprising the head and tail sequences and the target fragment.

The backbone oligonucleotide may comprise a custom sequence between the inverted repeat sequence, so that under the annealing conditions the backbone oligonucleotide forms a hairpin loop, as illustrated in FIG. 5.

As noted, probes may be designed so that the continuous strand of nucleic acid comprising the head and tail sequences and the target fragment is a linear strand of nucleic acid. Under annealing conditions in the presence of the target fragment, the head and tail sequences hybridise to the flanking sequences, defining a gap between the 5' end of the head sequence and the 3' end of the tail sequence. The target fragment hybridises to the target-complementary sequence in the gap, thereby positioning the ends of the target fragment in juxtaposition with the 5' end of the head sequence and the 3' end of the tail sequences, and completing a strand of nucleic acid which comprises the target fragment and the head and tail sequences. The nucleic acid molecules which form the strand have their ends in juxtaposition. The term juxtaposition has been discussed elsewhere. There is a nick between the ends to be ligated. Ligation of the ends produces the continuous strand of nucleic acid comprising at least the head and tail sequences and the target fragment.

Figure 6:
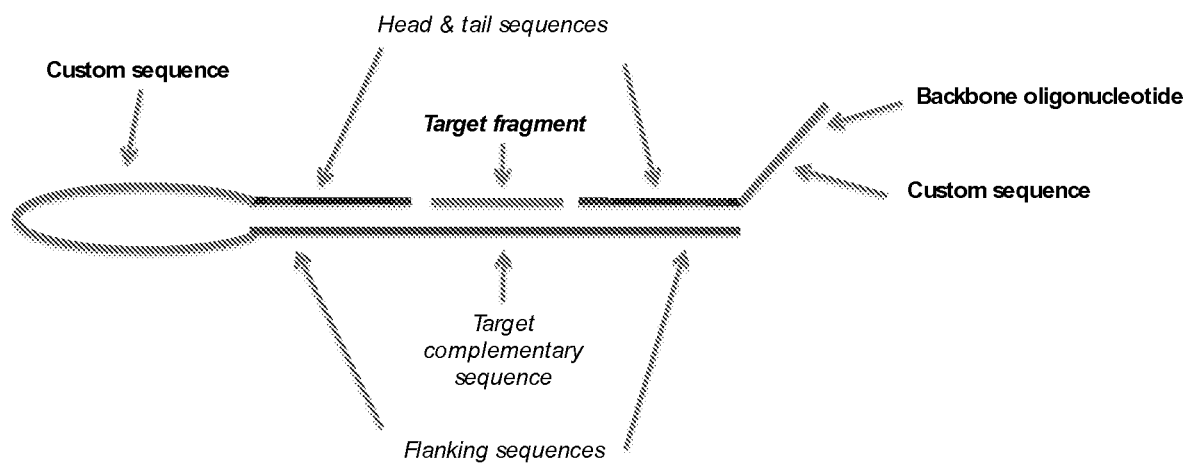
FIG. 6 shows a linear looped probe composed of a targeting oligonucleotide and a linear backbone oligonucleotide, with bound target fragment.

The probe may comprise a targeting oligonucleotide having the tail sequence at its 3' end and a linear backbone oligonucleotide having the head sequence at its 5' end. Under annealing conditions, the tail sequence binds in cis to the downstream flanking sequence of the targeting oligonucleotide, and the head sequence of the backbone oligonucleotide binds in trans to the upstream flanking sequence of the targeting oligonucleotide. The targeting oligonucleotide may comprise a custom sequence between the downstream flanking sequence and the tail sequence, so that under the annealing conditions the targeting oligonucleotide forms a hairpin loop. The linear strand of nucleic acid formed under annealing conditions comprises the backbone oligonucleotide, the target fragment and the targeting oligonucleotide. FIG. 6 illustrates this arrangement.

The probe may equally be arranged in the reverse orientation, where the head sequence is at the 5' end of the targeting oligonucleotide, and the probe comprises a backbone oligonucleotide having the tail sequence at its 3' end. In this case the head sequence binds in cis to the upstream flanking sequence of the targeting oligonucleotide and the tail sequence of the backbone oligonucleotide binds in trans to the downstream flanking sequence of the targeting oligonucleotide.

Figure 7:
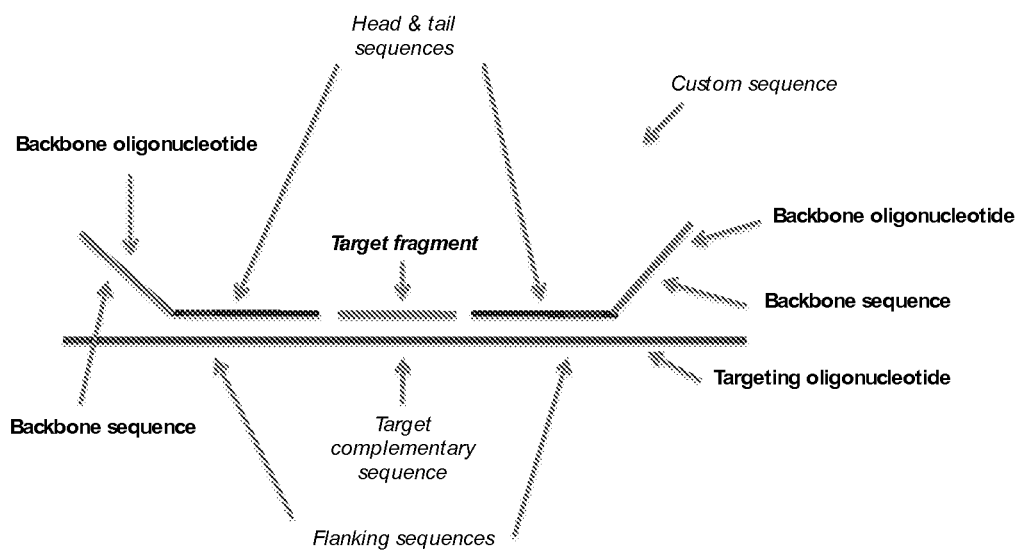
FIG. 7 shows a linear probe comprising two backbone oligonucleotides, with bound target fragment.

Another form of probe which forms a linear nucleic acid strand as the product of ligation is a probe comprising the head and tail sequences on separate backbone oligonucleotides. Such a probe may comprise a backbone oligonucleotide comprising a head sequence having a free 5' end, and a backbone oligonucleotide comprising a tail sequence having a free 3' end, wherein under the annealing conditions the head and tail sequences bind in trans to the flanking sequences of the targeting oligonucleotide. One or both backbone oligonucleotides may further comprise a custom sequence. FIG. 7 illustrates probes of this type.

Preferably, the oligonucleotides of the probe in its unligated form are linear. So, preferably the targeting oligonucleotide is a linear nucleic acid molecule. For probes including one or more backbone oligonucleotides, these are also preferably linear. This allows convenient differentiation between ligated and unligated probes where a circle of DNA is formed only as a result of successful ligation of the circularising embodiments of the probe. Linear nucleic acid molecules are not amplified by rolling circle replication.

Amplification of Products

Signal detection in the present method depends on signals being generated by or from correctly reacted probes following target recognition, using sequence specific hybridisation and enzymatic catalysis to generate specific products from which the signal is obtained. The present method uses detection of multiple loci on a nucleic acid species of interest target molecule as a signal amplification step, and therefore enables signal generation and detection without requiring amplification of the products of the reacted probes. Signals may be obtained and a cumulative signal may be detected without amplifying the ligation products. Optionally, however, the signal from the multiplex products may be amplified by traditional signal amplification steps.

A method may include enriching the ligation products before detection. Products may be enriched by amplification and/or by solid phase chemistry. Circular nucleic acid products may be selectively enriched by treating the sample with exonuclease (e.g., Lambda exonuclease) to digest linear nucleic acid products. In general, exonuclease degradation may be used to enrich for ligation products when the ligation products are protected from exonuclease degradation. Exonuclease should then be deactivated (e.g. by heat) before any subsequent step involving polymerisation, e.g. before rolling circle amplification. As illustrated in Example 2, 1 U Exonuclease may be added to remove non-reacted probes and fragments. Suitable conditions are incubation at 37° C. for 1 hour in corresponding exonuclease buffer, followed by enzyme inactivation at 80° C. for 20 minutes. Where capture/detect methods are used, ligation products may be enriched by capturing the products on a solid phase via the capture moiety. As illustrated in Example 1, a solution containing linear ligation products may be mixed with 10 ml M-280 streptavidin coated magnetic beads (Invitrogen) in Tris-HCl (pH 7.5), 3.5 mM EDTA and 0.07% Tween-20 in a final volume of 200 ml, and incubated at room temperature for 15 minutes. After incubation, the beads are collected using a ring magnet and supenatant is removed. Other ways of enriching for ligation products include specifically size-selecting ligation products.

Ligation products may be amplified by clonal amplification. Suitable amplification techniques include rolling circle amplification (see below), bridge PCR (Adessi C, et al., Nucleic Acids Res. 2000 Oct. 15; 28(20):E87), emulsion PCR (digital PCR in emulsions was described by Dressman et al., Proc Natl Acad Sci USA. 2003 Jul. 22; 100(15):8817-22. Epub 2003 Jul. 11) and digital PCR (Vogelstein & Kinzler, Proc Natl Acad Sci USA. 1999 Aug. 3; 96(16): 9236-41). Clonal localised amplification in gels was described by Mitra & Church, Nucleic Acids Res. 1999 Dec. 15; 27(24): e34. An embodiment of the present method may comprise amplifying the ligation products and obtaining a cumulative signal which is a combination of individual signals from the amplified products. Preferably, ligation products are amplified across the ligation junction or, for products of double ligation, across both ligation junctions.

Where the ligation products are circles of nucleic acid, amplification may comprise providing conditions for rolling circle replication of the circles of nucleic acid and detecting the products of rolling circle replication. Rolling circle replication was described in U.S. Pat. No. 5,854,033 (Lizardi) and Fire & Xu, Proc Natl Acad Sci USA. 1995 May 9; 92(10):4641-5. Rolling circle replication is an amplification of a circular nucleic acid molecule using a strand displacing DNA polymerase, resulting in large DNA molecules containing tandem repeats of the amplified sequence. The DNA polymerase catalyses primer extension and strand displacement in a processive rolling circle polymerisation reaction that proceeds as long as desired. It results in an amplification of the circularised probe sequence orders of magnitude higher than a single cycle of PCR replication and other amplification techniques in which each cycle is limited to a doubling of the number of copies of a target sequence. Additional amplification can be obtained using a cascade of strand displacement reactions. Rolling circle replication may be hyper branched rolling circle replication. Hyperbranched RCA was described by Lizardi et al., Nat Genet. 1998 July; 19(3):225-32. Conditions for rolling circle replication are illustrated in the Examples, for example incubation with 1 U of phi29 polymerase (New England Biolabs) can be added in corresponding phi29 buffer and nucleotides (dNTPs) at 37° C. for 1 hour.

Detection

Ligation products may be individually detectable, so that an individual signal is obtainable from the ligation products resulting from recognition of each target sequence by its corresponding probe. However, in the present method, the ligation products need not be individually detected. Individual signals from the ligation products are merged into a cumulative signal and the cumulative signal is detected.

The type of signal and the method of detection can be suitably chosen based upon the type of probe, or the probe may be designed to enable a desired signal type and detection method. The method is not limited to particular types of signal or signal detection means—rather, the method can be performed by any method of converting individual signals from the plurality of probes into a single cumulative detectable signal, thereby amplifying the individual signals through the multiplex nature of the probing step.

In general, detection of signals from ligation products is dependent on formation of each product following binding of the probe to its target sequence, thus indicating if the target sequence was present in the sample. Signals may thus be specifically obtained from products that include a ligation junction or, for products of double ligation, both ligation junctions. Individual signals may be obtainable from each ligation junction, formed as a result of probe hybridisation to each target sequence. So, for example, where a set of probes comprises 10 different probes that recognise 10 target sequences of the species of interest, there will be 10 ligation products including ligation junctions, and a cumulative signal may be detected, which is the combination of individual signals from the 10 ligation products. Of course, in this example the actual number of molecules probes, target sequences and ligation products may be higher than 10 because there will usually be multiple copies of each target sequence in a sample and the sample will be contacted with multiple copies of each probe.

Ligation products generated by probes of a set may produce individual signals characteristic of that set, and which differ from signals obtained from ligation products generated by probes of a different set, allowing the cumulative signals from each set of probes to be distinguished and separately quantified. For example, probes within a set can share a custom sequence which is common to that set and differs from the custom sequences of probes in other sets, allowing the probes from each set to be conveniently identified. Each set of probes may contain at least 500, 600, 700, 800, 900 or at least 1,000 different probes for binding a plurality of target sequences specific to the species of nucleic acid. For example, a method may use 1,000 different targeting oligonucleotides to each of chromosomes 21, 13 and 18, respectively, and three different sets of probes, each set labelled with a unique custom sequence, one for each chromosome. If desired, motifs encoding specific alleles and or loci can be incorporated in the custom sequence in high multiplex.

Relative quantities of the two or more chromosomes in a sample may be determined by detecting the cumulative signals from the products of double ligation from each of two or more sets of probes, each of which recognises target sequences specific to one chromosome, and quantifying the different cumulative signals.

A convenient way to obtain signals from the products of ligation is to provide conditions for amplification and to test for the presence of the amplification product. Several amplification approaches are possible, such as NASPA, LAMP, T7 amplification, PCR or, where the ligation product is a circle, rolling circle replication. Obtaining signals may involve amplification across a ligation junctions and detecting signals from the amplification products (e.g., by PCR or, for circularising embodiments of the probe, rolling circle replication), or capturing the continuous nucleic acid strand at one end and detecting its other end. Signals may be obtained from amplified or non-amplified ligation products using any of the conventional detection systems for nucleic acids such as detection of fluorescent labels, enzyme-linked detection systems, antibody-mediated label detection, and detection of radioactive labels. Preferably, a rolling circle amplification product is detected by hybridisation of a labelled detection oligonucleotide to a motif in the RCA product, e.g. a motif in a custom sequence of the probe. Because the amount of ligation product is directly proportional to the amount of target sequence present in a sample, quantitative measurements reliably represent the amount of a target sequence in a sample. Major advantages of this method are that the ligation step can be manipulated to obtain allelic discrimination, the DNA replication step is isothermal, and signals are strictly quantitative because the amplification reaction is linear and is catalysed by a highly processive enzyme. The primer oligonucleotide used for the DNA polymerase reaction can be the same for all probes of a set or for multiple sets of probes in a reaction mixture.

One example of signal detection employs a capture/label technique. Here, the ligation products comprise a capture moiety on one side of a ligation junction and a label on the other side of the ligation junction, and the method comprises obtaining signals from the ligation products by capturing the ligation products on a substrate via the capture moiety, washing the substrate and retaining a captured fraction comprising the substrate and captured ligation product, and detecting the labels on the ligation products in the captured fraction. Such methods are especially suitable where the ligation product is linear, so that one end of the product is captured and the other is detected. However, the methods can also be used where the ligation product is circular, by including a step of cleaving the circle to convert it to a linear product. The signal may be derived from a heterogeneous label or a sequence of the probe, e.g., custom sequence.

Fluorescent signals may be used, for example by labelling the probes of the first and second sets with different fluorescent labels. Thus, a method may comprise contacting the nucleic acid in the sample with a first set of probes and a second set of probes and detecting first and second cumulative signals, wherein the first cumulative signal is fluorescence at a first wavelength emitted by ligation products generated by probes of the first set, and wherein the second cumulative signal is fluorescence at a second wavelength emitted by ligation products generated by probes of the second set.

In some of these embodiments, the the products of the rolling circle replication of the ligation products generated by probes of the first and second sets are distinguishably labelled.

Capture/detect methods are particularly convenient for use with probes comprising separate nucleic acid molecules, (e.g. head and tail sequences on separate nucleic acid molecules). The ligation product then contains sequences of both molecules (e.g. the head and tail sequences) in a single nucleic acid molecule (the ligation product), whereas unligated probes do not. Accordingly, signals may be obtained from the ligation products by capturing the nucleic acid molecule containing the one sequence (e.g. head sequence), washing to remove unligated probe nucleic acid, then detecting the presence of the other sequence (e.g. tail sequence) in the captured fraction. Detection is specific to the ligated probes, since in unligated probes the two sequences are connected only by hybridisation between the nucleic acids and are separated by washing, whereas the ligated probes contain the two sequences on each side of a ligation junction in a continuous nucleic acid strand, i.e., covalently joined.

As noted, probes may be modified to carry capture moieties. The capture moiety may permit attachment to a solid substrate such as a bead. A suitable capture moiety is biotin, which pairs with streptavidin, allowing the modified probe nucleic acid to be isolated on the solid substrate coated with streptavidin. It may be convenient to provide the probe with the capture moiety before combining the probe with the sample. Alternatively, the capture moiety may be introduced after the ligation step.

Where a probe comprises a backbone oligonucleotide containing either the head or tail sequence, and a separate nucleic acid (targeting oligonucleotide, or a second backbone oligonucleotide) containing the tail or head respectively, either of these nucleic acid molecules may carry a capture moiety, for example may be biotinylated.

Where one nucleic acid molecule of a probe carries a capture moiety, the other may carry a label. It is possible to use the nucleic acid sequence itself as a label, detecting a custom sequence which identifies the nucleic acid molecules to be detected, e.g. is present in all probes of a set but not probes of another set. A complementary oligonucleotide may be used for detection. Alternatively the nucleic acid may carry a heterogeneous label such as a fluorophore. The heterogeneous label is not part of the nucleic acid itself. Other labels that can be used include quantum dots, bioluminescence, signal generating enzyme cascades like tyramide signal amplification, and radioactive moieties. The method may then comprise detecting the presence of the label, e.g., detecting fluorescence, detecting the quantum dots, detecting bioluminescence, detecting the signal generated by the enzyme, or detecting radioactivity, respectively.

As an example, obtaining signals from the ligation products may comprise capturing backbone oligonucleotides of the probes on a substrate via the capture moiety, washing the substrate to remove unligated probes and retaining a captured fraction comprising the substrate and captured backbone oligonucleotides, and obtaining signals from the products of double ligation in the captured fraction. Where the product of double ligation carries a label, this may comprise detecting the label in the captured fraction.

The capture moiety can be a biotin-molecule with affinity to a strepavidin-substrate. Other suitable affinity tags include polyhistidine-tags with affinity to immobilised metal ions, such as cobalt, nickel, copper which can be used for the purification of histidine containing sequences, e.g., backbone oligonucleotides. The capture moiety may thus be part of the sequence to be captured, e.g. a His-tag sequence, or it may be a heterogenous moiety which is not part of the nucleic acid itself.

A suitable solid substrate is a bead, for example magnetic beads to facilitate enrichment of the captured products using a magnet. The substrate may be coated with a binding member for the capture moiety, e.g. streptavidin coated magnetic beads may be used with biotinylated probes.

Quantifying

Quantification determines the amount of the species of nucleic acid in the sample. In some cases this amount may be determined and compared with a known control, enabling determination of the absolute or relative amount of nucleic acid in the sample. In other cases multiple species of nucleic acid may be probed within a sample, e.g., simultaneously. This enables one species of nucleic acid to be used as a reference, quantifying the different species of nucleic acid relative to each other, for example determining that a sample contains more of chromosome 21 than chromosome 1.

Quantity may be expressed as concentration or amount (e.g., moles or mass), the two being interchangeable where the concentration is the amount of nucleic acid divided by the volume of the sample.

Probes

Examples of probes and their features have already been described above. Some further features and examples are described here.

The probe nucleic acid is preferably DNA. However, it may be another nucleic acid, naturally occurring or not. The standard bases of DNA are A, T, C and G, but probe nucleic acid of the method may optionally include non-standard nucleotides.

In general, a probe for use in methods of the present method may comprise a targeting oligonucleotide and head and tail sequences. The head and tail sequences may be part of the targeting oligonucleotide, or one or both of them may be on a different nucleic acid molecule. Optionally, the probe comprises the targeting oligonucleotide, a backbone oligonucleotide comprising the head sequence and a backbone oligonucleotide comprising the tail sequence. A probe may therefore comprise one, two or three nucleic acid molecules in its non-ligated form.

Preferably, the probes are for hybridising to target sequences which are fragments of defined sequence generated from the species of nucleic acid to be quantified or identified. These target sequences may be referred to as target fragments.

The targeting oligonucleotide is longer than the target fragment and contains an internal target-complementary sequence, so that hybridisation between the targeting oligonucleotide and the target fragment forms a double stranded sequence located between upstream and downstream flanking sequences of the targeting oligonucleotide. The head and tail sequences have free 5' and 3' ends respectively, and are complementary to the upstream and downstream flanking sequences respectively. Under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences.

Probes of this type may be used to detect a species of nucleic acid in a method comprising:

(i) providing a sample in which the species of nucleic acid is fragmented into target fragments, (ii) providing denaturing conditions under which the target fragments are single stranded (iii) contacting the sample with a set of probes, wherein each probe specifically recognises a distinct target sequence within the species of nucleic acid to be detected, wherein the target sequences are sequences of the target fragments, and wherein each probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, (iv) providing annealing conditions under which the head and tail sequences hybridise to the flanking sequences, and target fragments, if present, hybridise to the target-complementary sequence of the probes, thereby positioning the ends of the target fragment in juxtaposition with the 5' end of the head sequence and the 3' end of the tail sequence (v) providing conditions for ligation so that, if a target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, and (vi) detecting a cumulative signal which is a combination of individual signals from all the products, wherein detection of the signal indicates the presence of the species of nucleic acid in the sample.

The species of nucleic acid may be quantified by a method comprising (i) providing a sample in which the species of nucleic acid is fragmented into target fragments (ii) providing denaturing conditions under which the target fragments are single stranded (iii) contacting the sample with a set of probes, wherein each probe specifically recognises a distinct target fragment of the species of nucleic acid to be quantified, wherein each probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, (iv) providing annealing conditions under which the head and tail sequences hybridise to the flanking sequences, and target fragments, if present, hybridise to the target-complementary sequence of the probes, thereby positioning the ends of the target fragment in juxtaposition with the 5' end of the head sequence and the 3' end of the tail sequence (v) providing conditions for ligation so that, if a target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, (vi) detecting a cumulative signal which is a combination of individual signals from all ligation products, and (vii) quantifying the cumulative signal to determine a signal level, wherein the signal level is proportional to the quantity of the species of nucleic acid in the sample, and thereby determining the quantity of the species of nucleic acid in the sample.

The method may be used to quantify a first species of nucleic acid relative to a second species of nucleic acid in a sample. Accordingly, the method may comprise (i) providing a sample in which the first and second species of nucleic acid are fragmented into target fragments (ii) providing denaturing conditions under which the target fragments are single stranded (iii) contacting the sample with a first set of probes and a second set of probes, wherein the probes of the first set specifically recognise distinct target fragments of the first species of nucleic acid and wherein probes of the second set specifically recognise distinct target fragments of the second species of nucleic acid, wherein each probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, (iv) providing annealing conditions under which the head and tail sequences hybridise to the flanking sequences, and target fragments, if present, hybridise to the target-complementary sequence of the probes, thereby positioning the ends of the target fragment in juxtaposition with the 5' end of the head sequence and the 3' end of the tail sequence (v) providing conditions for ligation so that, if a target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, (vi) detecting a first cumulative signal which is a combination of individual signals from the ligation products generated by probes of the first set, and quantifying it to determine a first signal level, wherein the first signal level is proportional to the quantity of the first species of nucleic acid in the sample, (vii) detecting a second cumulative signal which is a combination of individual signals from the ligation products generated by probes of the second set, and quantifying it to determine a second signal level, wherein the second signal level is proportional to the quantity of the second species of nucleic acid in the sample, and (viii) comparing the first and second signal levels, thereby determining the relative quantities of the first and second nucleic acid species in the sample.

The probes may be designed so that hybridisation of the target fragment in the gap completes a circle of nucleic acid, the circle comprising the target fragment and the head and tail sequences.

The head and/or tail sequence of the probe is preferably joined to a custom sequence which is not complementary to other regions of the probe or to the target fragment.

In some embodiments of the probe, a single nucleic acid molecule comprises the head and tail sequences.

The head and tail sequences may be separate from the targeting oligonucleotide so that they bind in trans to the flanking sequences. For example, the head and tail sequences may be at 5' and 3' ends respectively of a backbone oligonucleotide. A custom sequence can be included between the head and tail sequences of the backbone oligonucleotide. An example of such a probe is shown in FIG. 3. Alternatively, the head and tail sequences of the backbone oligonucleotide may be adjacent, with no intervening nucleotide sequence. In such a case, the flanking sequences of the targeting oligonucleotide hybridise along the full length of the backbone oligonucleotide and may circularise it.

The probes may be designed so that the head sequence is a 5' end of the targeting oligonucleotide and/or the tail sequence is a 3' end of the targeting oligonucleotide, so that hybridisation of the target fragment in the gap completes a strand of nucleic acid comprising the target fragment, the head and tail sequences, the target complementary sequence and the flanking sequences. The head and tail sequences may be at ends of the targeting oligonucleotide and bind in cis to the flanking sequences. An example of such a probe is shown in FIG. 4. In this version of the probe, the head and tail sequences and the target complementary sequence all become circularised with the target fragment. Custom sequences can be positioned in the loops of the oligonucleotide. The probe nucleic acid is relatively long but has the advantage of joining the oligonucleotide structure into one molecule that is pre-assembled and does not require hybridisation of different probe nucleic acid molecules.

Probes can also be designed with a backbone oligonucleotide, which is a separate molecule of nucleic acid from the targeting oligonucleotide. The tail sequence can be a 3' end of the targeting oligonucleotide and the head sequence a 5' end of a backbone oligonucleotide. Alternatively the head sequence can be a 5' end of the targeting oligonucleotide and the tail sequence a 3' end of a backbone oligonucleotide. A custom sequence can be introduced in the targeting oligonucleotide, for example to provide a loop between the head or tail sequence and the flanking sequence. An advantage with using this probe approach is that a detection sequence can be introduced in the loop and is associated with the target complementary sequence, which can be advantageous for multiplex methods, especially higher multiplexes with high-plex detection schemes. The backbone oligonucleotide can further comprise a custom sequence. By providing the probe in two oligonucleotides, the probe nucleic acid molecules are shorter than the single oligonucleotide version but maintain the same function.

Another design of the probe provides the head and tail sequences on two backbone oligonucleotides. Thus, the probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, a backbone oligonucleotide comprising a head sequence having a free 5' end, and a backbone oligonucleotide comprising a tail sequence having a free 3' end, wherein the head and tail oligonucleotide sequences are complementary to the upstream and downstream flanking sequences respectively.

One backbone oligonucleotide may carry a capture moiety, in which case the other backbone oligonucleotide is used for detection and may carry a heterogeneous label. One or both backbone oligonucleotides may further comprise a custom sequence. Alternatively or additionally, the targeting oligonucleotide may include a custom sequence.

Under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences. Hybridisation of the target fragment in the gap completes a strand of nucleic acid comprising the target fragment and the head and tail sequences. The strand carries the capture moiety and the label, permitting detection using the capture/detect methods described elsewhere herein.

Digital Karyotyping and Non-Invasive Pre-Natal Diagnosis

Some implementations of the present method provide particular advantages in fields where precise quantification of target DNA is sought. This includes a number of nucleic acid based diagnostic techniques. One such area is the analysis of cancer DNA in a biological sample (e.g., blood) from a patient. Another such area is non-invasive pre-natal diagnosis (NIPT) by analysis of cell free DNA.

A challenge with NIPT is that a large number of specific genome fragments must be counted in order to achieve the statistical confidence required to diagnose an chromosomal aneuploidies. Since the foetal DNA is mixed with the maternal DNA, making up 4-30% of the genetic material in a pregnant woman's bloodstream, observing a chromosomal aneuploidy in the foetal DNA requires a very precise measurement.

The present method may be used for analysing free circularising foetal DNA in samples of maternal blood. By using a plurality of probes directed to different fragments of one chromosome and a plurality of probes directed to different fragments of a second chromosome, the method enables an imbalance in the relative number of the two chromosomes in the sample to be determined with high confidence. This allows chromosomal aneuploidies such as trisomy to be diagnosed from foetal DNA even against the high background of the maternal DNA.

The present method may be used for, e.g., testing maternal blood samples from pregnant women to detect foetal nucleic acid for the diagnosis of chromosomal abnormalities such as trisomy, testing patient samples for tumour DNA for the diagnosis or monitoring of the presence of a tumour in the patient. Other uses include testing samples of material for the presence of microbial nucleic acid, where detection of the microbial nucleic acid indicates infection of the material by the microbe, which may be an infectious agent such as a bacterium, virus or fungus. The sample may be a tissue or blood sample from a patient.

More generally, by using hundreds or thousands of different probes, some implementations of the present method can achieve high precision by detecting hundreds or thousands of specific nucleic acid fragments, providing advantages across a range of diagnostic applications. Detecting a multitude of DNA fragments from the chromosome or chromosomal loci associated with a particular disease enables the amount of that chromosome or locus to be measured relative to a control chromosome or locus, so that even slight differences in a sample can be confidently detected.

By analysing short target fragments a large proportion of the highly fragmented cell free DNA in maternal blood can be analysed with high efficiency. This is important since very low amounts of cell free DNA are available in maternal blood.

A method of quantifying a first chromosome or chromosomal locus relative to a second chromosome or chromosomal locus in a sample of nucleic acid obtained from an individual may comprise contacting the sample with a first set of probes and a second set of probes, wherein the probes of the first set each specifically recognise a distinct target sequence within the first chromosome or chromosomal locus and wherein the probes of the second set each specifically recognise a distinct target sequence within the second chromosome or chromosomal locus, providing conditions under which the target sequences in the first and second chromosomes or chromosomal loci are at least partially single stranded, providing conditions for annealing and ligation, under which conditions the probes hybridise to their target sequences and generate ligation products, detecting a first cumulative signal which is a combination of individual signals from the ligation products generated by probes of the first set, and quantifying it to determine a first signal level, wherein the first signal level is proportional to the quantity of the first chromosome or chromosomal locus in the sample, detecting a second cumulative signal which is a combination of individual signals from the ligation products generated by probes of the second set, and quantifying it to determine a second signal level, wherein the second signal level is proportional to the quantity of the second chromosome or chromosomal locus in the sample, and comparing the first and second signal levels, thereby determining the relative quantities of the first and second chromosomes or first and second chromosomal loci in the sample.

The method may be used for diagnosing aneuploidy (e.g. trisomy) in a foetus, where the sample of nucleic acid is a sample obtained from maternal blood and contains cell free foetal DNA mixed with maternal DNA, and wherein an unequal ratio of the first and second signal levels is indicative of aneuploidy (e.g. trisomy).

EXAMPLES

The following examples are provided in order to demonstrate and further illustrate certain embodiments and aspects of the present invention and are not to be construed as limiting the scope thereof.

Example 1

This example illustrates detection and quantification of free circularising foetal DNA in maternal blood using the present method.

A blood sample is collected from the pregnant mother and free circularising DNA is extracted from the blood plasma. The DNA is then reacted with targeted specific DNA probes that specifically react with DNA fragments originating from the chromosomes subjected to analysis and quantification. In this example we illustrate the use of the so-called "Lotus probes" to target and react with specific fragments from chromosome 21 and a reference chromosome. However, other probe-based technologies for targeting specific DNA fragments could be used instead, such as padlock probes/Molecular Inversion Probes (MIPs), selector probes, oligonucleotide ligation probes.

Lotus probes are provided which target multiple fragments from each of two chromosomes. Upon target recognition, the probes generate a ligation product with their corresponding fragments, having one end labelled with fluorescence and the other with a biotin. The ligation products are labelled with two different fluorophores, each representing the individual chromosomes being targeted. The protocol can be illustrated as:
1) 10 ng of DNA is digested with 1 unit of restriction enzyme in corresponding compatible restriction enzyme buffer. The reaction is incubated in 37 C for 1 h, followed by enzymatic deactivation at 80° C. for 20 min.
2) The DNA fragments are denatured to single stranded fragments at 95° C. for 10 min and mixed with probes and ligase to form linear ligation products. The probe pool are added in 10 pM individual concentration along with 1 U of Ampligase (Epicentre) and incubated at 55° C. for 1 h in ligase buffer.
3) The ligation product is captured on magnetic streptavidin beads. To remove non-reacted probes and fragments, the solution is mixed with 10 ml M-280 streptavidin coated magnetic beads (Invitrogen) in Tris-HCl (pH 7.5), 3.5 mM EDTA and 0.07% Tween-20 in a final volume of 200 ml, and incubated at room temperature for 15 min. After incubation, the beads are collected using a ring magnet and supernatant removed.
4) The remaining bead-bound probes are detected and quantified. The total fluorescence intensity is measured for each of the two labels and the relative intensity is measured between the two colours.
5) In the case of prenatal diagnosis, the final result is based on the relative quantity of fluorescence. A simplified example; if 1000 genome equivalents and 10% of all free circularizing DNA in maternal blood is derived from the foetus, and 1000 chromosome 21 targeting probes are used to generate the total fluorescence, a normal sample would generate a signal of 1,000,000 fluorophores were as a sample with trisomy 21 foetus would generate a signal corresponding of 1,050,000 fluorophores. Also, to achieve higher statistical precision if 1000 probes are targeting "normalization" regions not subjected to aneuploidy, and labelled with a second fluorophore, a relative quantity can be measured.

Example 2

In the following example, the Lotus probes target multiple fragments from each of two chromosomes. Upon target recognition, the probes generate a circularised ligation product with their corresponding fragments. The circularised ligation products contain either of two sequence motifs that can be used for subsequent labelling, each sequence motif corresponding to either of the two chromosomes being targeted. The protocol can be illustrated as:
1) 10 ng of DNA is digested with 1 unit of restriction enzyme in corresponding compatible restriction enzyme buffer. The reaction is incubated in 37 C for 1 h, followed by enzymatic deactivation at 80° C. for 20 min.
2) The DNA fragments are denatured to single stranded fragments at 95° C. for 10 min and mixed with probes and ligase to form circles. The probe pool are added in 10 pM individual concentration along with 1 U of Ampligase (Epicentre) and incubated at 55° C. for 1 h in ligase buffer.
3) 1 U Exonuclease is added to remove non-reacted probes and fragments. I U of Lambda exonuclease (Epicentre) is added at 37 C for 1 h in corresponding exonuclease buffer followed by enzyme inactivation at 80° C. for 20 min.
4) The remaining circles are copied by rolling circle amplification, RCA. 1 U of phi29 polymerase (New England Biolabs) is added in corresponding phi29 buffer and nucleotides (dNTPs) at 37 C for 1 h. Probes complementary to the RCA-products, each labelled with either of two different fluorophores, are added to the RCA-mix. The resulting labelled RCA-products are counted individually and the relative number of RCA-products is measured between the two colours.
5) In the case of prenatal diagnosis, the final result is based on the relative quantity of fluorescence. A simplified example; if 1000 genome equivalents and 10% of all free circularizing DNA in maternal blood is derived from the foetus, and 1000 chromosome 21 targeting probes are used to generate the total fluorescence, a normal sample would generate a signal of 1,000,000 fluorophores were as a sample with trisomy 21 foetus would generate a signal corresponding of 1,050,000 fluorophores. Also, to achieve higher statistical precision if 1000 probes are targeting "normalization" regions not subjected to aneuploidy, and labelled with a second fluorophore, a relative quantity can be measured.

Example 3

Materials and Methods

Sample Preparation:
10 ml blood was collected from each subject into a cell-free DNA tube (Streck, Omaha, Nebr.). Plasma was isolated from blood by a double centrifugation protocol (1600 g for 10 min, followed by 16 000 g for 10 min, after a tube transfer following the first spin). cfDNA was isolated by the Qiagen ccf nucleic acid kit (Qiagen, Hilden, Germany) according to the manufacturer's protocol. The resulting DNA was eluted in 50 ul of buffer (part of the Qiagen kit).

Probe and Backbone Design:

The multiplexed probe technology herein described enables specific and simultaneous amplification of thousands of chromosomal fragments. Probes were designed to capture 2500-5000 fragments (targets) from each of chromosomes 21, 18, and 13. Targets were selected to have unique sequence in the genome, uniformed AT/GC composition, not include known polymorphism nor CNVs in target sequence, and a size between 18-35 bp. Probes targeting 2500 fragments from each chromosome 13 and 18 were pooled together with 5000 probes targeting fragments from chromosome 21 to create a single oligo probe pool.

Example sequence of probes, "N" represents target complementary sequence:
(SEQ ID NO: 1)
ATGTGACCCTTCCGTCTGTTGAGTTAGGCCNNNNNNNNNNNNNNNNNNNN

NNNNNNNNNNNTCGTGCCTTGTCATTCGGGAGCACTAACTGCTG

The backbones, with head and tail sequences complementary to the ends of the probe, were designed to include sequence motifs for both sequencing and digital counting. Two backbones were used in the experiments outlined in the result section; one complementary to probes targeting chromosome 13 and 18:

SEQ ID NO: 2
(/5Phos/CGCACACGATTAAGGTCCAGTCACAGGCAGAGATCGGAAGAG

CGTCGTGTAGGGAAAGAGTGTNNNNNNNNNNNGTGTAGATCTCGGTGGTCG

CCGTATCATTTCATGCTGCTAACGGTCGAGTCGGACAGGTGGCTCCACTA

AATAGACGCA);, and one backbone targeting chromosome 21:

(/5Phos/GGCCTAACTCAACAGACGGAAGGGTCACATAGATCGGAAGAG

CGTCGTGTAGGGAAAGAGTGTNNNNNNNNNNNGTGTAGATCTCGGTGGTCG

CCGTATCATTTCATGCTGCTAACGGTCGAGCAGTTAGTGCTCCCGAATGA

CAAGGCACGA; SEQ ID NO: 3).

Biochemistry Probe Protocol:

50 ul of purified cfDNA was digested with 5 U of MseI (New England Biolabs) in 1×NEB4 buffer (New England Biolabs) and 1×BSA in a total volume of 55 ul at 37 C in 30 min followed by heat inactivation at 65 C in 20 min. The digested DNA was then mix with ligation mix along with probes and backbones. The 55 ul of digested DNA was mixed with probes (1 pM/probe), backbones (60 nM each), 1× ligation buffer (Epicentre), 100 U of Ampligase (Epicentre), 1 mM NAD, and 5 mM $Mg^{2+}$ to a total volume of 70 ul. The digested fragments were first denatured to single stranded DNA at 95 C in 5 min followed by 55 C hybridization and ligation in 16 h. The ligation mix was then treated with exonucleases to remove any remaining linear DNA molecules. The ligation reaction was mixed with 20 U of ExoI (NEB) and 5 U of ExoIII (NEB) and 1×BSA tot total volume of 75 ul at 37 C for 60 min followed by heat inactivation at 65 C for 10 min.

Analysis:

For sequencing analysis, the exo treated circles was amplified with sequencing primers complementary to the Illumina sequencing instrument and subsequently loaded on the Illumina Miseq instrument according to manufacturers protocol.

For digital analysis, the exo treated reactions was subjected to a rolling circle amplification reaction (RCA) to generate discrete DNA objects of concatemeric copies of the circle. 37.5 ul of exo treated circles were mixed with 4 mM DTT, 3 U of phi29 polymerase (NEB), 0.1 uM primer, 1 mM dNTP mix (NEB) and 1×BSA in a total volume in 50 ul, and incubated at 37 C for 1 h followed by a heat inactivation at 65 C for 10 min. The RCA reaction was then labeled with fluorescently labeled oligonucleotides complementary to the backbone sequence. 50 ul of RCA products was mixed with 0.1% Tween 20 (Sigma), 5 nM labeled oligonucleotides, and 2×SSC (Sigma) in a total volume of 100 ul. The labeled RCA-products were finally deposited on a microscope slide coated with Poly-lysine (Sigma) and counted in a fluorescent microscope.

Results

The probe method herein described was demonstrated on Illumina sequencing and a digital counting system. To demonstrate the performance of the probe method, a DNA sample with trisomy 21 was mixed with DNA extracted from normal plasma samples (3-5 ml plasma) in different concentrations. The samples was then carried through the probe method and evaluated by sequencing.

Figure 8:
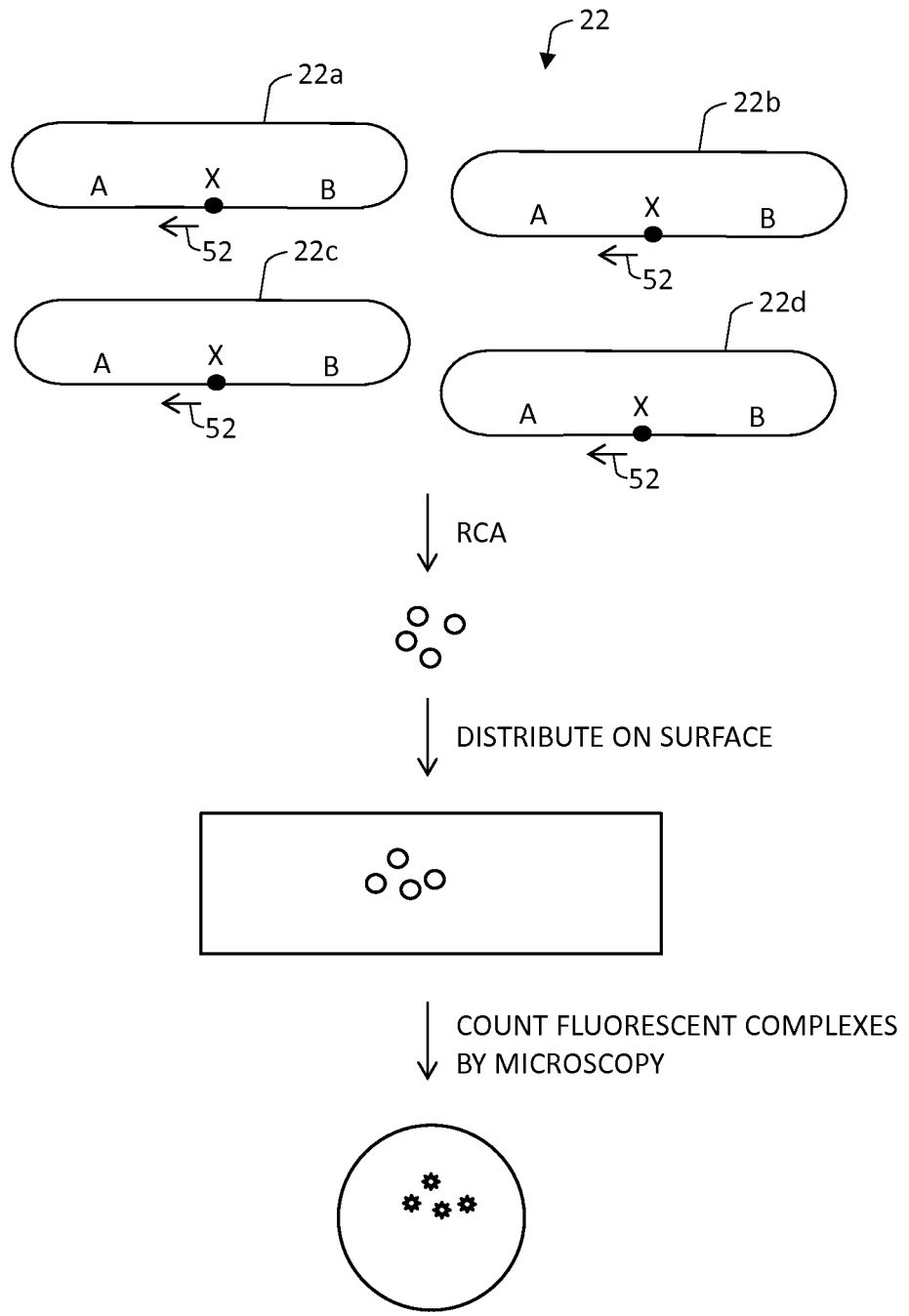
FIG. 8 shows a method by which RCA products can be counted.

For the results shown in FIG. 8, 100 ng of cell line DNA was subjected to the protocol described above. 10,000 probes were mixed in a pool to specifically circularize 10,000 corresponding chromosomal fragments from chromosome 13, 18, and 21. The 10,000 resulting circles were then amplified with Illumina-corresponding PCR primers and analyzed on gel prior sequencing. Lane 1 corresponds to DNA ladder, lane 2 the DNA sample after digestion, and lane 3 the PCR product with 10,000 amplified fragments.

Figure 9:
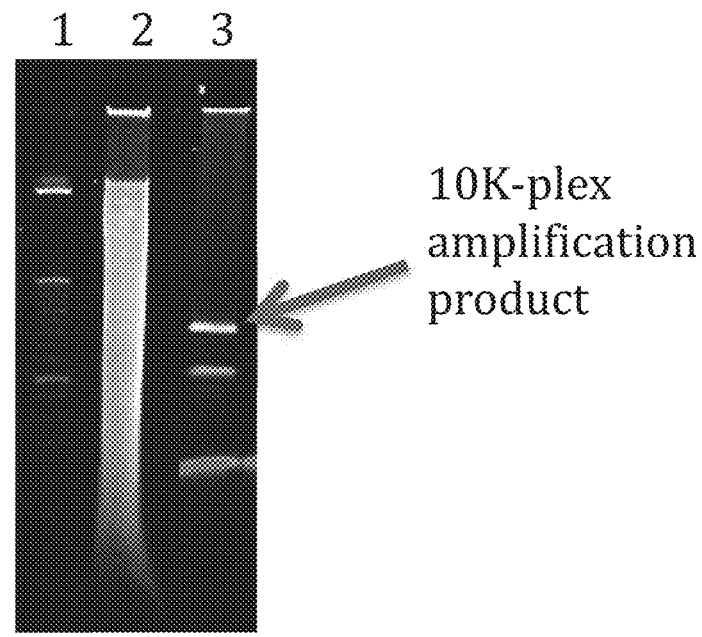
FIG. 9 is an image of a gel showing the specificity of the method described herein.
Figure 10:
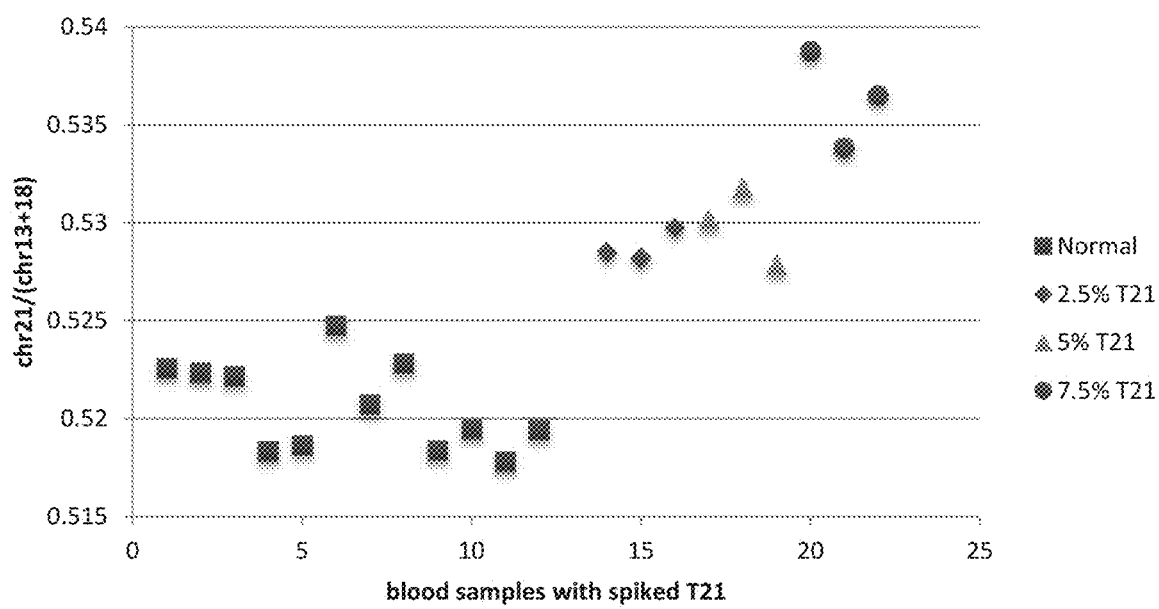
FIG. 10 is a graph showing the precision of the method described herein.
Figure 11:
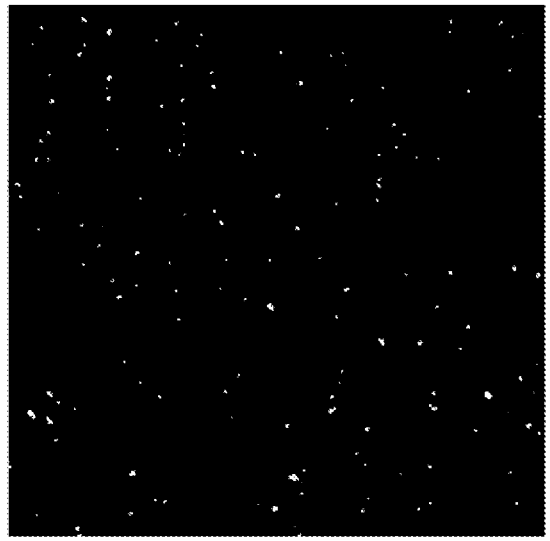
FIG. 11 panel A shows an image of labeled RCA products on the surface of a slide; panel B shows how ratios of fragments from different chromosomes can be accurately determined by counting individual RCA products.
Figure 11:
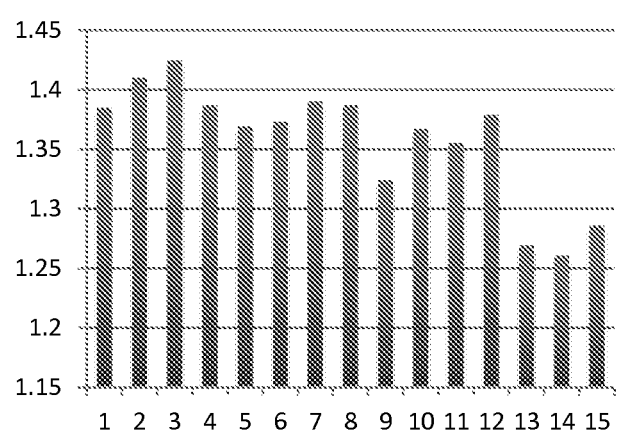

For the results shown in FIG. 9, 12 normal plasma samples were analyzed in parallel with samples carry DNA with trisomy 21 in different concentrations. DNA were extracted and processed through the 10K-plex probe protocol and finally sequenced on Illumina sequencer. Using a confidence interval providing 99% specificity, the positive samples are detected with a 90% sensitivity based on the estimated normal distributions.

FURTHER STATEMENTS

The following clauses represent aspects of the invention and are part of the description.

1. A method of detecting a species of nucleic acid in a sample, comprising contacting the sample with a set of probes, wherein each probe specifically recognises a distinct target sequence within the species of nucleic acid to be detected, providing conditions under which the target sequences in the species of nucleic acid are at least partially single stranded, providing conditions for annealing and ligation, under which conditions the probes hybridise to their target sequences and generate ligation products, each ligation product comprising a ligation junction, and detecting a cumulative signal which is a combination of individual signals from all ligation products, wherein detection of the signal indicates the presence of the species of nucleic acid in the sample.

2. A method of quantifying a species of nucleic acid in a sample, comprising contacting the sample with a set of probes, wherein each probe specifically recognises a distinct target sequence within the species of nucleic acid to be quantified, providing conditions under which the target sequences in the species of nucleic acid are at least partially single stranded, providing conditions for annealing and ligation, under which conditions the probes hybridise to their target sequences and generate ligation products, each ligation product comprising a ligation junction, and detecting a cumulative signal which is a combination of individual signals from all ligation products, quantifying the cumulative signal to determine a signal level, wherein the signal level is proportional to the quantity of the species of nucleic acid in the sample, and thereby determining the quantity of the species of nucleic acid in the sample.

3. A method of quantifying a first species of nucleic acid relative to a second species of nucleic acid in a sample, comprising contacting the sample with a first set of probes and a second set of probes, wherein the probes of the first set each specifically recognise a distinct target sequence within the first species of nucleic acid and wherein the probes of the second set each specifically recognise a distinct target sequence within the second species of nucleic acid, providing conditions under which the target sequences in the first and second species of nucleic acid are at least partially single stranded, providing conditions for annealing and ligation, under which conditions the probes hybridise to their target sequences and generate ligation products, each ligation product comprising a ligation junction, detecting a first cumulative signal which is a combination of individual signals from the ligation products generated by probes of the first set, and quantifying it to determine a first signal level, wherein the first signal level is proportional to the quantity of the first species of nucleic acid in the sample, detecting a second cumulative signal which is a combination of individual signals from the ligation products generated by probes of the second set, and quantifying it to determine a second signal level, wherein the second signal level is proportional to the quantity of the second species of nucleic acid in the sample, and comparing the first and second signal levels, thereby determining the relative quantities of the first and second nucleic acid species in the sample.

4. A method according to any of the preceding clauses, wherein the target sequences are non-overlapping.

5. A method according to any of the preceding clauses, wherein the set of probes comprises at least 10 probes that each specifically recognise a distinct target sequence.

6. A method according to clause 5, wherein the set of probes comprises at least 100 probes that each specifically recognise a distinct target sequence.

7. A method according to clause 6, wherein the set of probes comprises at least 1,000 probes that each specifically recognise a distinct target sequence.

8. A method according to clause 7, wherein the set of probes comprises at least 10,000 probes that each specifically recognise a distinct target sequence.

9. A method according to any of the preceding clauses, comprising amplifying the ligation products and obtaining a cumulative signal which is a combination of individual signals from the amplified products.

10. A method according to clause 9, wherein the amplification is clonal amplification.

11. A method according to clause 9 or clause 10 comprising amplifying the ligation products across the ligation junction.

12. A method according to any of the preceding clauses, wherein the ligation products are products of double ligation, each comprising first and second ligation junctions.

13. A method according to clause 12, wherein the method comprises amplifying the ligation products across the first and second ligation junctions.

14. A method according to any of clauses 1 to 8, comprising obtaining a cumulative signal which is a combination of individual signals from the ligation products without amplifying the ligation products.

15. A method according to any of clauses 1 to 13, wherein the ligation products are circles of nucleic acid.

16. A method according to clause 15, comprising providing conditions for rolling circle replication of the circles of nucleic acid and detecting the products of rolling circle replication.

17. A method according to clause 16, wherein the rolling circle replication is hyper branched rolling circle replication.

18. A method according to any of clauses 1 to 14, wherein the ligation products are linear nucleic acids.

19. A method according to clause 18, wherein the ligation products comprise a capture moiety on one side of a ligation junction and a label on the other side of the ligation junction, and the method comprises obtaining signals from the ligation products by capturing the ligation products on a substrate via the capture moiety, washing the substrate and retaining a captured fraction comprising the substrate and captured ligation product, and detecting the labels on the ligation products in the captured fraction.

20. A method according to any of the preceding clauses, wherein the signal is fluorescence.

21. A method according to clause 20, comprising contacting the nucleic acid in the sample with a first set of probes and a second set of probes and detecting first and second cumulative signals, wherein the first cumulative signal is fluorescence at a first wavelength emitted by ligation products generated by probes of the first set, and wherein the second cumulative signal is fluorescence at a second wavelength emitted by ligation products generated by probes of the second set.

22. A method according to any of the preceding clauses, wherein the probes are ligated to generate the ligation products.

23. A method according to clause 22, wherein the probes and the target sequences are ligated to generate the ligation products.

24. A method according to any of the preceding clauses, wherein the ligation products are circles of nucleic acid comprising the target sequences.

25. A method according to any of the preceding clauses, wherein the species of nucleic acid is fragmented.

26. A method according to clause 25, wherein the target sequences are sequences of fragments of the species of nucleic acid.

27. A method according to clause 25 or clause 26, wherein the sample is a restriction enzyme digest of nucleic acid and the target sequence is a restriction fragment.

28. A method according to any of clauses 25 to 27, wherein the probe is ligated to each end of the target sequence.

29. A method according to clause 28, wherein the probes each comprise a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, wherein under the conditions for annealing and ligation, the head and tail sequences hybridise to the flanking sequences, and the target fragment, if present, hybridises to the target-complementary sequence, thereby positioning the ends of the target fragment in juxtaposition with the 5' end of the head sequence and the 3' end of the tail sequence, wherein the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment.

30. A method according to clause 29, wherein the sample of fragmented nucleic acid is a restriction enzyme digest and the target fragment is a restriction fragment.

31. A method according to clause 28 or clause 29, wherein the step of detecting the product of double ligation comprises providing conditions for amplification across the first and second ligation junctions of the continuous strand of nucleic acid, and detecting whether an amplification product is present.

32. A method according to any of clauses 29 to 31, wherein the continuous strand of nucleic acid comprising the head and tail sequences and the target fragment is a circle of nucleic acid.

33. A method according to clause 32, wherein the step of detecting the product of double ligation comprises providing conditions for rolling circle replication and detecting whether a product of rolling circle replication is present.

34. A method according to clause 33, wherein the rolling circle replication is hyper branched rolling circle replication.

35. A method according to any of clauses 32 to 34, wherein the probe comprises the head and tail sequences on one nucleic acid molecule.

36. A method according to clause 35, wherein the probe comprises a backbone oligonucleotide having the head and tail sequences at its 5' end 3' ends respectively, wherein the head and tail sequences of the backbone oligonucleotide bind in trans to the flanking sequences of the targeting oligonucleotide under the annealing conditions.

37. A method according to clause 36, wherein the backbone oligonucleotide comprises a custom sequence between the head and tail sequences, wherein the custom sequence is not complementary to other regions of the probe or to the target fragment.

38. A method according to clause 36, wherein the head and tail sequences of the backbone oligonucleotide are adjacent.

39. A method according to any of clauses 32 to 35, wherein the head and tail sequences are at ends of the targeting oligonucleotide and bind in cis to the flanking sequences under the annealing conditions.

40. A method according to clause 39, wherein the targeting oligonucleotide comprises a custom sequence between the targeting oligonucleotide and the head and/or tail sequence, wherein the custom sequence is not complementary to other regions of the probe or to the target fragment.

41. A method according to any of clauses 29 to 34, wherein the tail sequence is at the 3' end of the targeting oligonucleotide, and the probe comprises a backbone oligonucleotide having the head sequence at its 5' end, wherein under the annealing conditions the tail sequence binds in cis to the downstream flanking sequence of the targeting oligonucleotide, and the head sequence of the backbone oligonucleotide binds in trans to the upstream flanking sequence of the targeting oligonucleotide.

42. A method according to clause 41, wherein the backbone oligonucleotide comprises a pair of inverted repeat sequences, wherein under the annealing conditions the inverted repeat sequences form a hairpin structure, thereby positioning the 3' end of the backbone oligonucleotide in juxtaposition with the 5' end of the targeting oligonucleotide, and wherein under the conditions for ligation, the 5' end of the targeting oligonucleotide is ligated to the 3' end of the backbone oligonucleotide, so that the product of double ligation is a circle of nucleic acid comprising the targeting oligonucleotide, the target fragment and the backbone oligonucleotide.

43. A method according to any of clauses 29 to 34, wherein the head sequence is at the 5' end of the targeting oligonucleotide, and the probe comprises a backbone oligonucleotide having the tail sequence at its 3' end, wherein under the annealing conditions the head sequence binds in cis to the upstream flanking sequence of the targeting oligonucleotide, and the tail sequence of the backbone oligonucleotide binds in trans to the downstream flanking sequence of the targeting oligonucleotide.

44. A method according to clause 43, wherein the backbone oligonucleotide comprises a pair of inverted repeat sequences, wherein under the annealing conditions the inverted repeat sequences form a hairpin structure, thereby positioning the 5' end of the backbone oligonucleotide in juxtaposition with the 3' end of the targeting oligonucleotide, and wherein under the conditions for ligation, the 3' end of the targeting oligonucleotide is ligated to the 5' end of the backbone oligonucleotide, so that the product of double ligation is a circle of nucleic acid comprising the targeting oligonucleotide, the target fragment and the backbone oligonucleotide.

45. A method according to any of clauses 41 to 44, wherein the backbone oligonucleotide comprises a custom sequence between the inverted repeat sequence, so that under the annealing conditions the backbone oligonucleotide forms a hairpin loop.

46. A method according to any of clauses 29 to 33 wherein the continuous strand of nucleic acid comprising the head and tail sequences and the target fragment is a linear strand of nucleic acid.

47. A method according to clause 46, wherein the tail sequence is at the 3' end of the targeting oligonucleotide, and the probe comprises a backbone oligonucleotide having the head sequence at its 5' end, wherein under the annealing conditions the tail sequence binds in cis to the downstream flanking sequence of the targeting oligonucleotide, and the head sequence of the backbone oligonucleotide binds in trans to the upstream flanking sequence of the targeting oligonucleotide.

48. A method according to any of clauses 41, 42 or 47, wherein the targeting oligonucleotide comprises a custom sequence between the downstream flanking sequence and the tail sequence, so that under the annealing conditions the targeting oligonucleotide forms a hairpin loop.

49. A method according clause 46, wherein the head sequence is at the 5' end of the targeting oligonucleotide, and the probe comprises a backbone oligonucleotide having the tail sequence at its 3' end, wherein under the annealing conditions the head sequence binds in cis to the upstream flanking sequence of the targeting oligonucleotide, and the tail sequence of the backbone oligonucleotide binds in trans to the downstream flanking sequence of the targeting oligonucleotide.

50. A method according to any of clauses 43, 44 or 49, wherein the targeting oligonucleotide comprises a custom sequence between the head sequence and the upstream flanking sequence, so that under the annealing conditions the targeting oligonucleotide forms a hairpin loop.

51. A method according to any of clauses 41 to 45 or 47 to 50, wherein the backbone oligonucleotide carries a capture moiety.

52. A method according to clause 46, wherein the probe comprises a backbone oligonucleotide comprising a head sequence having a free 5' end, and a backbone oligonucleotide comprising a tail sequence having a free 3' end, wherein under the annealing conditions the head and tail sequences bind in trans to the flanking sequences of the targeting oligonucleotide.

53. A method according to clause 52, wherein one or both backbone oligonucleotides further comprise a custom sequence, wherein the custom sequence is not complementary to other regions of the probe or to the target fragment.

54. A method according to clause 52 or clause 53, wherein one of the backbone oligonucleotides carries a capture moiety.

55. A method according to clause 54, wherein the other backbone oligonucleotide carries a heterogeneous label.

56. A method according to clause 55, wherein the label is a fluorophore.

57. A method according to clause 51 or any of clauses 54 to 56, wherein the step of detecting whether the product of double ligation is present comprises capturing the backbone oligonucleotide on a substrate via the capture moiety, washing the substrate to remove unligated probes and retaining a captured fraction comprising the substrate and captured backbone oligonucleotide, and testing for the presence of the product of double ligation in the captured fraction.

58. A method according to clause 55 or clause 56, wherein the step of detecting whether the product of double ligation is present comprises capturing the backbone oligonucleotide on a substrate via the capture moiety, washing the substrate to remove unligated probes and retaining a captured fraction comprising the substrate and captured backbone oligonucleotide, and testing for the presence of the label in the captured fraction.

59. A method according to clause 51 or any of clauses 54 to 58, wherein the capture moiety is biotin.

60. A method according to any of clauses 29 to 59, wherein the target-complementary sequence has a length of 10 to 30 nucleotides.

61. A method according to any clauses 29 to 60, wherein the target-complementary sequence has fewer than 5 base pair mismatches with the target fragment.

62. A method according to clause 61, wherein the target-complementary sequence is the exact complement of the target fragment.

63. A method according to any of clauses 29 to 62 clause, wherein the flanking sequences each have a length of 10 to 30 nucleotides.

64. A method according to any of clauses 29 to 63, wherein the upstream and downstream flanking sequences are different from each other.

65. A method according to any of clauses 29 to 64 clause, wherein the head sequence has fewer than 5 base pair mismatches with the upstream flanking sequence and the tail sequence has fewer than 5 base pair mismatches with the downstream flanking sequence.

66. A method according to clause 65, wherein the head sequence is the exact complement of the upstream flanking sequence and the tail sequence is the exact complement of the downstream flanking sequence.

67. A method according to any of clauses 29 to 66, wherein the targeting oligonucleotide is linear.

68. A method according to any of clauses 29 to 67 clause, wherein the sample is a sample of fragmented human chromosomes.

69. A method according to clause 68, wherein the species of nucleic acid is a chromosome and the target sequences are human genome fragments specific to that chromosome.

70. A method according to clause 68, wherein the species of nucleic acid is a chromosomal locus and the target fragments are specific to that locus of the human genome.

71. A method according to any of the preceding clauses, wherein the probe nucleic acid is DNA.

clause 72. A method according to clause 68 or clause 69, wherein the method comprises contacting a sample of fragmented chromosomes with a set of probes for binding multiple fragments of a chromosome, wherein each probe in the set is for binding a different target fragment specific to that chromosome.

73. A method according to clause 72, wherein the probes share a common custom sequence.

74. A method according to any of the preceding clauses, wherein the method comprises contacting a sample of fragmented chromosomes with two or more sets of probes for binding multiple fragments of two or more chromosomes, comprising:

a first set of probes is for binding a plurality of target fragments specific to a first chromosome, and a second set of probes is for binding a plurality of target fragments specific to a second chromosome, and optionally one or more further bsets of probes for binding a plurality of target fragments specific to one or more further chromosomes.

75. A method according to clause 74, wherein each set of probes comprises at least 500 different probes for binding a plurality of target fragments specific to the chromosome.

76. A method according to clause 74 or clause 75, wherein the probes within a set share a custom sequence which is common to that set and differs from the custom sequences of probes in other sets.

77. A method according to clause 76, comprising determining the relative quantities of the two or more chromosomes in the sample by detecting and quantifying cumulative signals from the custom sequences in the products of double ligation for each set of probes.

78. A method according to any of clauses 72 to 77, wherein the chromosome or chromosomes are human.

79. A method according to clause 28, wherein the probes comprise double stranded selector constructs, each individual selector comprising one or two protruding end sequences complementary to the ends of the target fragments, wherein under the conditions for annealing and ligation, the end sequences of the selectors hybridise to the end sequences of the fragments and are ligated to the selectors.

80. A method according to clause 22, wherein the probes are padlock probes, each comprising a linear oligonucleotides with target complementary sequences at the ends and a non-target complementary sequence in between, wherein under the conditions for annealing and ligation, the target complementary sequences are brought together head to tail to hybridise to adjacent regions of the target sequence and are ligated form a circle of nucleic acid.

81. A method according to any of the preceding clauses, wherein the species of nucleic acid is a chromosome or chromosomal locus.

82. A method according to any of the preceding clauses, wherein the sample is a blood or tissue sample.

83. A method according to clause 82, wherein the sample contains a mix of foetal and maternal DNA from the blood of a pregnant woman.

84. A method according to clause 81 or clause 82, wherein the species of nucleic acid to be detected or quantified is tumour-associated DNA.

85. A method according to clause 81 or clause 82, wherein the species of nucleic acid to be detected or quantified is microbial DNA.

86. A method of quantifying a first chromosome or chromosomal locus relative to a second chromosome or chromosomal locus in a sample of nucleic acid obtained from an individual, comprising contacting the sample with a first set of probes and a second set of probes, wherein the probes of the first set each specifically recognise a distinct target sequence within the first chromosome or chromosomal locus and wherein the probes of the second set each specifically recognise a distinct target sequence within the second chromosome or chromosomal locus, providing conditions under which the target sequences in the first and second chromosomes or chromosomal loci are at least partially single stranded, providing conditions for annealing and ligation, under which conditions the probes hybridise to their target sequences and generate ligation products, detecting a first cumulative signal which is a combination of individual signals from the ligation products generated by probes of the first set, and quantifying it to determine a first signal level, wherein the first signal level is proportional to the quantity of the first chromosome or chromosomal locus in the sample, detecting a second cumulative signal which is a combination of individual signals from the ligation products generated by probes of the second set, and quantifying it to determine a second signal level, wherein the second signal level is proportional to the quantity of the second chromosome or chromosomal locus in the sample, and comparing the first and second signal levels, thereby determining the relative quantities of the first and second chromosomes or first and second chromosomal loci in the sample.

87. A method according to clause 83 or clause 86, for diagnosing trisomy in a foetus, wherein the sample of nucleic acid is a sample of cell free foetal DNA obtained from the mother's blood, and wherein an unequal ratio of the first and second signal levels is indicative of trisomy.

88. A nucleic acid probe for binding a single stranded target nucleic acid fragment, wherein the probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively so that under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences, and wherein hybridisation of the target fragment in the gap completes a circle of nucleic acid, the circle comprising the target fragment and the head and tail sequences.

89. A nucleic acid probe according to clause 88, wherein the head and/or tail sequence is joined to a custom sequence, wherein the custom sequence is not complementary to other regions of the probe or to the target fragment.

90. A nucleic acid probe according to clause 88 or clause 89, wherein a single nucleic acid molecule comprises the head and tail sequences.

91. A probe according to clause 88 or clause 89, wherein the head and tail sequences are separate from the targeting oligonucleotide and bind in trans to the flanking sequences.

92. A probe according to clause 91, wherein the head and tail sequences are at 5' and 3' ends respectively of a backbone oligonucleotide.

93. A probe according to clause 92, wherein the backbone oligonucleotide comprises a custom sequence between the head and tail sequences, wherein the custom sequence is not complementary to other regions of the probe or to the target fragment.

94. A probe according to clause 92, wherein the head and tail sequences of the backbone oligonucleotide are adjacent. 95. A nucleic acid probe for binding a single stranded target nucleic acid fragment, wherein the probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail oligonucleotide sequences are complementary to the upstream and downstream flanking sequences respectively so that under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences, and wherein the head sequence is a 5' end of the targeting oligonucleotide and/or the tail sequence is a 3' end of the targeting oligonucleotide, so that hybridisation of the target fragment in the gap completes a strand of nucleic acid comprising the target fragment, the head and tail sequences, the target complementary sequence and the flanking sequences.

96. A probe according to clause 88 or clause 95, wherein the head and tail sequences are at ends of the targeting oligonucleotide and bind in cis to the flanking sequences.

97. A probe according to clause 88 or clause 95, wherein the tail sequence is a 3' end of the targeting oligonucleotide and the head sequence is a 5' end of a backbone oligonucleotide separate from the targeting oligonucleotide.

98. A probe according to clause 88 or clause 95, wherein the head sequence is a 5' end of the targeting oligonucleotide and the tail sequence is a 3' end of a backbone oligonucleotide separate from the targeting oligonucleotide.

99. A probe according to clause 97 or clause 98, wherein the backbone oligonucleotide further comprises a custom sequence, wherein the custom sequence is not complementary to other regions of the probe or to the target fragment.

100. A nucleic acid probe for binding a single stranded target nucleic acid fragment, wherein the probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, a backbone oligonucleotide comprising a head sequence having a free 5' end, and a backbone oligonucleotide comprising a tail sequence having a free 3' end, wherein the head and tail oligonucleotide sequences are complementary to the upstream and downstream flanking sequences respectively, and wherein one backbone oligonucleotide carries a capture moiety and the other backbone oligonucleotide carries a heterogeneous label, so that under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences, and wherein hybridisation of the target fragment in the gap completes a strand of nucleic acid comprising the target fragment and the head and tail sequences, wherein the strand carries the capture moiety and the label.

101. A probe according to clause 100, wherein the capture moiety is biotin.

102. A probe according to clause 100 or clause 101, wherein the label is a fluorophore.

103. A probe according to any of clauses 100 to 102, wherein one or both backbone oligonucleotides further comprise a custom sequence, wherein the custom sequence is not complementary to other regions of the probe or to the target fragment.

104. A probe according to any of clauses 88 to 103, wherein the targeting oligonucleotide further comprises a custom sequence which is not complementary to other regions of the probe or to the target fragment.

105. A probe according to any of clauses 88 to 104 clause, wherein the target-complementary sequence has a length of 10 to 30 nucleotides.

106. A probe according to any of clauses 88 to 105, wherein the target-complementary sequence has fewer than 5 base pair mismatches with the target fragment.

107. A probe according to clause 106, wherein the target-complementary sequence is the exact complement of the target fragment.

108. A probe according to any of clauses 88 to 107, wherein the flanking sequences each have a length of 10 to 30 nucleotides.

109. A probe according to any of clauses 88 to 108, wherein the upstream and downstream flanking sequences of the targeting oligonucleotide are different from each other.

110. A probe according to any of clauses 88 to 109, wherein the head sequence has fewer than 5 base pair mismatches with the upstream flanking sequence and the tail sequence has fewer than 5 base pair mismatches with the downstream flanking sequence.

111. A probe according to clause 110, wherein the head and tail sequences are the exact complement of the flanking sequences.

112. A probe according to any of clauses 88 to 111, wherein the targeting oligonucleotide is linear.

113. A probe according to any of clauses 88 to 112, wherein the target fragment is a restriction endonuclease fragment.

114. A probe according to any of clauses 88 to 113, wherein the target fragment is a human genome fragment.

115. A probe according to clause 114, wherein the target fragment is a human genome fragment specific to one chromosome.

116. A probe according to clause 115, wherein the target fragment is specific to one locus of the human genome.

117. A probe according to any of clauses 88 to 116, wherein the probe nucleic acid is DNA.

118. A set of probes for binding single stranded target nucleic acid fragments, comprising a plurality of probes according to any of clauses 88 to 117, the probes having a plurality of different target-complementary sequences for the binding multiple different target fragments.

119. A set of probes according to clause 118 which is for binding multiple fragments of a human chromosome, wherein each probe in the set is for binding a different target fragment specific to that chromosome.

120. A set of probes according to clause 119, wherein the probes share a common custom sequence.

121. Sets of probes for binding different fragments of two or more human chromosomes, comprising:

a first set of probes for binding a plurality of target fragments specific to a first chromosome, and a second set of probes for binding a plurality of target fragments specific to a second chromosome, and optionally one or more further sets of probes for binding a plurality of target fragments specific to one or more further chromosomes.

122. Sets of probes according to clause 121, wherein the probes within a set share a custom sequence which is common to that set and differs from the custom sequences of probes in other sets.

123. A kit comprising a set or sets of probes according to any of clauses 118 to 122 in solution in one or more containers.

124. Use of a probe according to any clauses 88 to 117, a set or sets of probes according to any of clauses 118 to 122, or a kit according to clause 123, for testing a sample for the presence of a species of nucleic acid.

125. Use of a set of probes for testing a sample for the presence of target fragments obtained from a species of nucleic acid, wherein each probe of the set comprises a targeting oligonucleotide containing a sequence which is the exact complement of a target fragment, and head and tail oligonucleotide sequences which hybridise adjacent to the target fragment on the targeting oligonucleotide, wherein hybridisation between the target fragment and the probe templates the target fragment for ligation to the head and tail sequences.

An embodiment provides a method of sample analysis, comprising:

a) hybridizing a sample comprising fragmented DNA with a probe mix comprising a first set of probes, wherein the probes of the first set of probes:
  i. hybridize to different sites in a first chromosome; and
  ii. form non-covalently circular products containing ligatably adjacent junctions when hybridized to DNA fragments from the first chromosome;
b) ligating the ligatably adjacent junctions together to produce a plurality of covalently circular ligation products;
c) amplifying the covalently circular ligation products by rolling circle amplification (RCA) to produce a plurality of RCA product molecules;
d) labeling the RCA product molecules; and
e) quantifying the number of labeled RCA product molecules produced in step d), thereby providing an estimate of the amount of DNA corresponding to the first chromosome in the sample.

In any embodiment, the first chromosome may be chromosome 21, 13 or 18.

In any embodiment, the probe mix may comprises a second set of probes, wherein the probes of the second set of probes hybridize to different sites in a second chromosome and form non-covalently circular products containing ligatably adjacent junctions when hybridized to DNA fragments from the second chromosome; and step e) comprises separately quantifying the number of rolling circle amplification product molecules that correspond to the first and second chromosomes, thereby providing an estimate of the relative amount of DNA corresponding to the first and second chromosomes in the sample.

In some embodiments, the first set of probes hybridize to different sites in a first region of a first chromosome. In these embodiments, the probe mix may comprises a second set of probes, wherein the probes of the second set of probes hybridize to different sites in a second region in the first chromosome and form non-covalently circular products containing ligatably adjacent junctions when hybridized to DNA fragments from the second chromosome; and step e) comprises separately quantifying the number of rolling circle amplification product molecules that correspond to the first and second regions of the first chromosomes, thereby providing an estimate of the relative amount of DNA corresponding to the first and second regions of the first chromosome in the sample.

In any embodiment, the first chromosome is chromosome 21 and the second chromosome is selected from chromosome 13 and chromosome 18.

In any embodiment, each of the non-covalently circular products comprises a fragment of DNA from the sample. In these embodiments, the probes of step a) may comprise:
  i. a head sequence and a tail sequence, wherein the head and tail sequences are at the ends of a first oligonucleotide molecule; and
  ii. a splint sequence comprising, in order:
    an upstream flanking sequence that is complementary to the head sequence;
    a target complementary sequence that is complementary to a target fragment; and
    a downstream flanking sequence that is complementary to the tail sequence;
  and, in the non-covalently circular products, the ends of the target fragment are ligatably adjacent to the ends of the head and tail sequences in the first oligonucleotide molecule.

In these embodiments, the splint sequence may be in the first oligonucleotide molecule. Alternatively, the splint sequence may be in a second oligonucleotide molecule.

In any embodiment, the sample may digested with a restriction enzyme.

In any embodiment, the sample comprises genomic DNA, e.g., cell-free DNA isolated from blood.

In any embodiment, the sample may comprise cell-free DNA isolated from the bloodstream of a pregnant human.

In any embodiment, the chromosome may be isolated from a tissue biopsy.

In any embodiment, the chromosome may be a microbial chromosome.

In any embodiment, the quantifying step may be done by separating individual rolling circle amplification product molecules produced in step c) from one another, and counting the number of individual rolling circle amplification product molecules in a defined area or volume.

In these embodiments, the quantifying step may be done by:
  i. hybridizing a labeled oligonucleotide to the RCA product molecules, wherein the labeled oligonucleotide hybridizes to a sequence that is repeated in the RCA product, thereby producing a plurality of complexes that each comprise a single RCA product and a plurality of labeled oligonucleotides that are hybridized to the RCA product; and
  ii. counting the number of labeled complexes.

In these embodiments, the quantifying step may be done by:
  (a) obtaining a substrate comprising the labeled complexes distributed on the surface of the substrate; and
  (b) counting the number of RCA products that are present in the first area of the substrate.

In these embodiments, the method may comprise:
  (a) obtaining a substrate comprising a first and second pluralities of complexes distributed on the surface of the substrate, wherein each of the complexes comprises a single RCA product and a plurality of labeled oligonucleotide probes that are hybridized to the RCA product, the first and second pluralities of complexes are distinguishably labeled, and the first and second pluralities of complexes correspond to different chromosomes; and
  (b) counting the number of the first plurality of RCA products and, independently, counting the number of the second plurality of RCA products, that are present in the first area of the substrate. In this embodiment, the oligonucleotides may be fluorescently labeled.

In these embodiments, the first set of probes may comprise at least 50 probes.

What is claimed is:

1. A method of quantifying a first chromosome or chromosomal locus relative to a second chromosome or chromosomal locus in a sample comprising fragments of human genomic DNA, comprising:

contacting the sample with a first set of probes and a second set of probes, wherein the probes each comprise:

(a) a targeting oligonucleotide comprising: (i) an internal target-complementary sequence that is in the range of 10 to 30 nucleotides in length and complementary to a fragment of the human genomic DNA, (ii) an upstream flanking sequence that is in the range of 10 to 30 nucleotides in length and not complementary to human genomic DNA, and (iii) a downstream flanking sequence that is in the range of 10 to 30 nucleotides in length and not complementary to human genomic DNA, and (b) a second oligonucleotide comprising a head sequence and a tail sequence having free 5' and 3' ends respectively, wherein the head sequence and the tail sequence are complementary to the upstream flanking sequence and the downstream flanking sequence, respectively, and wherein the probes of the first set each specifically recognise a distinct target sequence within the first chromosome or chromosomal locus and wherein the probes of the second set each specifically recognise a distinct target sequence within the second chromosome or chromosomal locus, providing conditions under which the target sequences in the first and second chromosome or chromosomal locus are at least partially single stranded, providing conditions for annealing and ligation, under which conditions the probes hybridise to their target sequences and generate ligation products, each ligation product being a circle of nucleic acid comprising the second oligonucleotide and a fragment of human genomic DNA that is in the range of 10 to 30 nucleotides in length, providing conditions for rolling circle amplification of the circles of nucleic acid, labelling the rolling circle amplification products in solution by hybridizing them to labelled oligonucleotides to produce hybridized labelled rolling circle amplification products, distributing the hybridized labelled rolling circle amplification products on the surface of a support;

counting the number of first rolling circle amplification products on the support, wherein the first rolling circle amplification products are amplified from the ligation products generated by probes of the first set and labelled by a first label, to provide a first count, counting the number of second rolling circle amplification products on the support, wherein the second rolling circle amplification products are amplified from the ligation products generated by probes of the second set and labelled by a second label, to provide a second count, and comparing the first and second counts, thereby determining the relative quantities of the first chromosome or chromosomal locus relative to a second chromosome or chromosomal locus in the sample.

2. The method of claim 1, wherein the first chromosome is chromosome 21 and the second chromosome is selected from chromosome 13 and chromosome 18.

3. The method of claim 1, wherein the set of probes comprises at least 10 probes that each specifically recognise a distinct target sequence.

4. The method according to claim 3, wherein the set of probes comprises at least 100 probes that each specifically recognise a distinct target sequence.

5. The method according to claim 4, wherein the set of probes comprises at least 1,000 probes that each specifically recognise a distinct target sequence.

6. The method according to claim 5, wherein the set of probes comprises at least 10,000 probes that each specifically recognise a distinct target sequence.

7. The method of claim 1, wherein the ligation products are products of double ligation, each comprising first and second ligation junctions.

8. The method of claim 1, wherein the counting steps are done by separating individual rolling circle amplification product molecules from one another, and counting the number of individual rolling circle amplification product molecules in a defined area or volume.

9. The method of claim 8, wherein the counting step is done by:
(i) hybridizing a labelled oligonucleotide to the RCA product molecules, wherein the labelled oligonucleotide hybridizes to a sequence that is repeated in the RCA product, thereby producing a plurality of complexes that each comprise a single RCA product and a plurality of labelled oligonucleotides that are hybridized to the RCA product; and
(ii) counting the number of labelled complexes.

10. The method according to claim 9, wherein the counting step is done by:
(a) obtaining a substrate comprising the labeled complexes distributed on the surface of the substrate; and
(b) counting the number of RCA products that are present in the first area of the substrate.

11. The method of claim 1, wherein the rolling circle amplification products are individually counted by:
(a) obtaining a substrate comprising a plurality of complexes distributed on the surface of the substrate, wherein each of the complexes comprises a single RCA product and a plurality of labelled oligonucleotide probes that are hybridized to the RCA product, and wherein the complexes corresponding to the first rolling circle amplification products and the complexes corresponding to the second rolling circle amplification products are distinguishably labelled; and
(b) counting the number first RCA products and, independently, counting the number of second RCA products, that are present in an area of the substrate.

12. The method of claim 1, wherein the sample is a blood or tissue sample.

13. The method according to claim 12, wherein the sample contains a mix of foetal and maternal DNA from the blood of a pregnant woman.

14. The method according to claim 12, wherein the chromosome or chromosomal locus to be detected or quantified is tumour-associated DNA.

15. The method of claim 1, wherein the species of nucleic acid to be detected or quantified is microbial DNA.

* * * * *